(12) United States Patent
Geissler et al.

(10) Patent No.: US 9,175,166 B2
(45) Date of Patent: Nov. 3, 2015

(54) MULTI-LAYER METALLIC EFFECT PIGMENTS, PROCESS FOR THEIR PREPARATION AND USE

(75) Inventors: Bernhard Geissler, Schwarzenbruck (DE); Wolfgang Herzing, Neunkirchen am Sand (DE); Jasmin Bleisteiner, Kirchensittenbach (DE); Martin Fischer, Königstein (DE); Ralph Schneider, Lauf (DE)

(73) Assignee: ECKART GMBH (DE)

( * ) Notice: Subject to any disclaimer, the term of this patent is extended or adjusted under 35 U.S.C. 154(b) by 1193 days.

(21) Appl. No.: 12/670,007

(22) PCT Filed: Jul. 24, 2008

(86) PCT No.: PCT/EP2008/006084
§ 371 (c)(1),
(2), (4) Date: Jan. 21, 2010

(87) PCT Pub. No.: WO2009/012995
PCT Pub. Date: Jan. 29, 2009

(65) Prior Publication Data
US 2010/0196296 A1    Aug. 5, 2010

(30) Foreign Application Priority Data
Jul. 24, 2007 (DE) .......................... 10 2007 034 928

(51) Int. Cl.
*C09C 1/00* (2006.01)
*A61K 8/11* (2006.01)
(Continued)

(52) U.S. Cl.
CPC ................ *C09C 1/0021* (2013.01); *A61K 8/11* (2013.01); *A61Q 1/02* (2013.01); *C08K 9/02* (2013.01);
(Continued)

(58) Field of Classification Search
CPC .............. A61K 2800/412; A61K 2800/436; A61K 8/11; A61Q 1/02; A61Q 1/06; A61Q 3/02; C01P 2004/20; C01P 2004/54; C01P 2004/61; C01P 2006/60; C01P 2006/62; C01P 2006/63; C01P 2006/64; C01P 2006/65
USPC .................................. 106/403, 404, 415, 417
See application file for complete search history.

(56) References Cited

U.S. PATENT DOCUMENTS 2,839,378 A    6/1958    McAdow
2,941,894 A    6/1960    McAdow
(Continued)

FOREIGN PATENT DOCUMENTS

DE    10 2004 002 222 B3    7/2006
DE    10 2004 063433 A1    7/2006
(Continued)

OTHER PUBLICATIONS

International Search Report dated Nov. 26, 2008, issued in corresponding international application No. PCT/EP2008/006084.
(Continued)

*Primary Examiner* — Shuangyi Abu Ali
(74) *Attorney, Agent, or Firm* — Ostrolenk Faber LLP

(57) ABSTRACT

A metallic effect pigment comprising at least three layers:
A) a layer A which comprises at least one metal $M_A$ and has an average oxygen content $O_A$, based on the total amount of $M_A$ and $O_A$ in the layer A,
B) a layer B comprising at least one metal $M_B$ and having an average oxygen content $O_B$ of 0 to 77 atom %, more particularly of 0 to 58 atom %, based on the total amount of $M_B$ and $O_B$ in the layer B,
C) a layer C which comprises at least one metal $M_C$ and has an average oxygen content $O_C$, based on the total amount of $M_C$ and $O_C$ in the layer C,
the average oxygen content $O_{AC}$ in layers A and C being determined in accordance with the formula (I)

$$O_{AC} = \frac{1}{2}\left(\frac{O_A}{M_A + O_A} + \frac{O_C}{M_C + O_C}\right) \quad (I)$$

and being situated within a range from 2 to 77 atom %, more particularly from 25 to 58 atom %. The disclosure further relates to processes for preparing this effect pigment and also to its use.

44 Claims, 18 Drawing Sheets

(51) Int. Cl.
*A61Q 1/02* (2006.01)
*C08K 9/02* (2006.01)
*C09C 1/62* (2006.01)
*C09C 1/64* (2006.01)
*C09D 5/03* (2006.01)
*C09D 5/36* (2006.01)
*C09D 7/12* (2006.01)
*C09D 11/037* (2014.01)
*C09D 11/322* (2014.01)
*A61Q 1/06* (2006.01)
*A61Q 3/02* (2006.01)
*C08K 3/08* (2006.01)

(52) U.S. Cl.
CPC . *C09C 1/62* (2013.01); *C09C 1/642* (2013.01); *C09D 5/035* (2013.01); *C09D 5/36* (2013.01); *C09D 7/1225* (2013.01); *C09D 7/1266* (2013.01); *C09D 7/1275* (2013.01); *C09D 11/037* (2013.01); *C09D 11/322* (2013.01); *A61K 2800/412* (2013.01); *A61K 2800/436* (2013.01); *A61Q 1/06* (2013.01); *A61Q 3/02* (2013.01); *C01P 2004/20* (2013.01); *C01P 2004/54* (2013.01); *C01P 2004/60* (2013.01); *C01P 2004/61* (2013.01); *C01P 2006/62* (2013.01); *C01P 2006/63* (2013.01); *C01P 2006/64* (2013.01); *C01P 2006/65* (2013.01); *C08K 3/08* (2013.01); *C08K 2201/014* (2013.01); *C09C 2200/1037* (2013.01); *C09C 2200/20* (2013.01); *C09C 2200/30* (2013.01); *C09C 2200/308* (2013.01); *C09C 2200/502* (2013.01); *C09C 2200/505* (2013.01); *Y10T 428/12056* (2015.01); *Y10T 428/12549* (2015.01)

(56) References Cited

U.S. PATENT DOCUMENTS

| | | | |
|---|---|---|---|
| 3,438,796 A | | 4/1969 | Hanke |
| 4,321,087 A | | 3/1982 | Levine et al. |
| 4,430,366 A | | 2/1984 | Crawford et al. |
| 5,364,467 A | * | 11/1994 | Schmid et al. ............... 106/404 |
| 5,505,991 A | * | 4/1996 | Schmid et al. ............... 427/215 |
| 5,571,624 A | | 11/1996 | Phillips et al. |
| 5,624,486 A | * | 4/1997 | Schmid et al. ............... 106/404 |
| 5,766,827 A | | 6/1998 | Bills et al. |
| 2006/0034787 A1 | * | 2/2006 | Bujard ............................ 424/63 |
| 2006/0118663 A1 | | 6/2006 | Herzing |
| 2008/0102269 A1 | * | 5/2008 | Herzing et al. ............... 428/336 |
| 2009/0013906 A1 | | 1/2009 | Fischer et al. |

FOREIGN PATENT DOCUMENTS

| | | |
|---|---|---|
| EP | 0259592 B1 | 11/1990 |
| EP | 0 747 453 A | 12/1996 |
| EP | 1 522 606 A | 4/2005 |
| WO | WO 99/35194 | 7/1999 |
| WO | WO 2004/026971 | 4/2004 |
| WO | WO 2004/026972 | 4/2004 |
| WO | WO 2004/052999 A2 | 6/2004 |
| WO | WO 2007/093401 A | 8/2007 |

OTHER PUBLICATIONS

German Office Action dated Apr. 3 2008, issued in corresponding German priority application No. DE 10 2007 034 928.0.
*Pigment Handbook*: "Properties and Economics." vol. 1, $2^{nd}$ ed. 1973 S. 807ff, Wiley-Interscience.
Rodriguez, A.B.J., "Metallic flop and its measurement." JOCCA, 1992 (4) S. 150-153.

* cited by examiner

1. Oxygen source 1
2. Metal vaporization source

MULTI-LAYER METALLIC EFFECT PIGMENTS, PROCESS FOR THEIR PREPARATION AND USE

CROSS REFERENCE TO RELATED APPLICATIONS

The present application is a 35 U.S.C. §371 National Phase conversion of PCT/EP2008/006084, filed Jul. 24, 2008, which claims the benefit of German Application No. 10 2007 034 928.0, filed Jul. 24, 2007, the disclosure of which is incorporated herein by reference. The PCT International Application was published in the German language.

TECHNICAL FIELD

The present invention relates to a multilayer, mirrorlike, metallically lustrous effect pigment and also to processes for preparing the same. The invention further relates to the use of these effect pigments in various areas of application.

BACKGROUND

Metallic effect pigments have been used for many years in coatings in order to generate a metallic effect.

Conventional metallic effect pigments consist of platelet-shaped metallic pigments whose effect derives from the directed reflection of incident light from metal particles of planar form which are oriented in parallel in the respective application medium.

Typical fields of application of metallic effect pigments are the coatings industry, especially the automotive industry, the printing industry, and the plastics industry.

The metallic effect is described by certain parameters. These parameters include the brilliance (sparkle and metallic luster), the lightness, and the flop (change in lightness as a function of incident angle and/or viewing angle), and the covering power. In the case of colored metallic coatings, further parameters are the chroma and the color flop ("two-tone").

The gloss is determined according to the proportion of reflected to scattered light in relation to a standard.

Key factors influencing the metallic effect include the particle morphology and the form factor (ratio of average particle diameter to average particle thickness) of the pigments, the thickness of the particles and also their surface roughness, the particle size, the particle-size distribution, and the orientation of the pigment parallel to the surface of the coating material or plastic.

In relatively large-diameter pigment particles of uniform morphology the reflection is relatively high, this being manifested in high metallic brilliance, improved lightness, and strong flop, whereas, for relatively low-particle-diameter pigments, the scattering fraction is very high, resulting in good covering power.

The covering power is determined above all, however, by the thickness of the metallic pigments. The thinner the metallic pigments, the better their specific covering power, i.e., the covering power per unit weight.

On the part of the printing, coatings, plastics, and cosmetics industries there is great interest in colored metallic pigments, and particularly in metallic pigments with a golden luster. Products resembling gold possess a high esthetic quality and give the materials thus coated, printed or colored a valuable appearance.

In recent times, however, black metallic effects as well have been enjoying increasing popularity. For instance, the color black has presently become the fashion color in the automobile sector. These effects are based on mixtures of black pigments with conventional aluminum pigments. Metallic pigments which are inherently black and also have a high gloss have not so far made a commercial entrance.

Very well established are the pigments known as gold bronze powders, which consist predominantly of copper/zinc alloys and which depending on composition may have different hues from red gold to rich gold (Pigment Handbook, vol. 1, 1973, p. 807 ff., Wiley-Interscience). Gold bronze pigments are produced by atomization of a liquid copper/zinc alloy melt and subsequent milling of the powder formed during atomization. In the course of the milling operation, the alloy particles are deformed to a platelet shape and comminuted. In the art, gold bronze pigments are obtained predominantly by dry milling. In order to avoid instances of cold welding, lubricant such as stearic acid, for example, is added to the atomized powder employed. Irregularities on the surface and edges of the metal platelets have the effect of reducing luster. These conventionally manufactured metallic effect pigments possess not only a pronounced particle-size distribution but also particle thicknesses of well above 100 nm.

For higher-value applications, particularly thin aluminum pigments have been developed, which are produced via PVD techniques.

Metallic pigments produced by PVD techniques have been known for some considerable time. They are notable for extremely high gloss, an enormous covering power, and unique optical properties. Owing to their low thickness of around 30 to 70 nm and their extremely smooth surfaces, they have a tendency, following application, to conform very closely to the substrate. If the substrate itself is very smooth, the result is virtually a mirrorlike appearance.

Of the pure metallic pigments, only aluminum pigments have made a commercial entrance to date. Examples thereof are Metalure® (manufactured by Avery Dennison, sold by ECKART), Decomet® (Schlenk) or Metasheen® (Ciba). Such pigments represent the "silver" hue in its highest embodiment.

High-value colored metallic effects are generally obtained by blending PVD aluminum pigments with dyes and/or color pigments. In this way, for example, it is possible to generate high-value gold hues by blending the PVD aluminum pigments with yellow dyes or color pigments. Such blends, however, have disadvantages: for instance, these blends cannot be applied in particular to absorbent substrates, owing to the separation there of metallic pigment from dye. In applications requiring high light fastnesses, these systems often fail because of the deficient light fastness of the colored pigment or of the dye.

Pigments based on metallic layers and produced via PVD techniques are described in more detail in U.S. Pat. No. 2,839,378.

Described therein is the manufacture of mirrorlike pigments with extremely thin layer thicknesses, which are applied by vapor deposition to a substrate provided with a "release layer". After the metal layers have been applied and the film detached, the pigments are comminuted to the desired particle size by means of mechanical action.

The application of pigments manufactured in this way in coating formulations is described in detail in U.S. Pat. No. 2,941,894. That patent emphasizes the high reflectivities, the low level of pigmentation, and the high hiding power or covering power of the pigments.

The operation of producing metallic pigments by means of vapor deposition processes with a thickness of 35 to 45 nm is described with greater precision in U.S. Pat. No. 4,321,087, and involves the application of a release coat, the metallizing operation, the detachment operation in a solvent bath, the concentrating of the particles, and their ultrasonic comminution to the desired pigment size.

These one-layer metallic pigments have a limited diversity of hue. There is a need for new color effects with optically high-grade metallic pigments.

WO2004/026971 and WO2004/026972 relate to one-layer, high-luster, golden metallic effect pigments which are composed of a copper-based alloy and other metallic alloying constituents and are manufactured by detachment and comminution of metal films deposited under vacuum. The disadvantages of such pigments are the limited diversity of hue. The manufacture of pigments using Cu or Zn as heavy metal leads to pigments which have a high density and, in association therewith, a relatively low covering power, and also leads to sedimentation problems in certain formulations. Another disadvantage lies in the high sensibility of these alloy pigments to corrosion.

Multilayer effect pigments manufactured by PVD techniques (Physical Vapor Deposition) have also been known for a long time. They were first described in U.S. Pat. No. 3,438,796. Claimed therein are five-layer interference pigments having a central, reflecting aluminum layer, flanked on either side by an $SiO_2$ layer with a thickness of 100 to 600 nm and, lastly, by semitransparent absorber layers comprising aluminum. The central aluminum layer is to have a reflecting effect, i.e., layer thicknesses of more than 60 nm are needed for this purpose. The external aluminum absorber layers, in contrast, must possess layer thicknesses of below 40 nm in order to have semitransparency properties. In that patent, furthermore, an interference pigment having a three-layer construction was described, in which a central $SiO_2$ layer is flanked by two thin, semitransparent aluminum layers.

U.S. Pat. No. 5,571,624 claims a paint which comprises multicolor interference pigments. These pigments possess a central metallic reflecting layer, flanked on either side by layer stacks composed in turn of a dielectric and a semiopaque metal layer, the dielectric layer facing the reflector core. Here again, in order to be truly opaque, the central metallic reflecting layer is required to have a minimum thickness of 35 to 40 nm. The dielectric layers ought to possess at least an optical layer thickness of two quarters of a selected wavelength of 400 nm. For an $SiO_2$ layer, for example, with a refractive index of 1.55, this corresponds to a geometric minimum layer thickness of 310 nm.

Golden metallic pigments of high quality are disclosed in DE 10 2004 063433 A1. Described therein are multilayer PVD pigments which have a central metal layer so thin that it no longer has an opaquely reflecting effect. On either side this layer is coated with dielectric layers. The manufacture of these kind of pigments is inevitably expensive, since producing a pigment layer on the detachment foil requires the latter to be coated three or five times. The production of the absorbing central layer cannot easily be reproduced under production conditions.

Similar pigments are disclosed in WO 2004/052999 A2. They have the same disadvantages.

These multilayer effect pigments all have the disadvantage that the dielectric layers, in comparison to metal layers, can be applied by vapor deposition only at very slow rates. Consequently, multilayer effect pigments produced by vaporization techniques, in which dielectrics are vaporized or vapor-deposited, can be produced only very cost-intensively. Furthermore, a foil has to be vapor-coated a plurality of times in order for the multilayer structure to be realizable, and this pushes the manufacturing costs up further.

EP 1 522 606 A1 describes the production of a foil with black aluminum oxide. Neither effect pigments nor multilayer structures are disclosed therein. The films disclosed there have no notable metallic effect with luster and flop.

U.S. Pat. No. 4,430,366 describes the production of films which comprise a mixture of metal and metal oxide. Here again, no effect pigments are mentioned. The films possess an inhomogeneous composition with a gradient of metal and metal oxide over the layer thickness, the metal concentration gradient and the metal oxide gradient being contrary to one another.

SUMMARY

It is an object of the invention to provide highly brilliant, colored or black, mirrorlike metallic effect pigments with very high optical qualities and very high light/dark flop.

It is an object of the invention, moreover, to provide, in particular, highly brilliant, golden, mirrorlike metallic effect pigments with very high esthetic quality, without color bleeding.

A further object is to find inexpensive preparation processes for providing such metallic pigments.

The object on which the invention is based is achieved through provision of a multilayer PVD effect pigment, the metallic effect pigment comprising at least three layers:

A) a layer A which comprises at least one metal $M_A$ and has an average oxygen content $O_A$, based on the total amount of $M_A$ and $O_A$ in the layer A, B) a layer B comprising at least one metal $M_B$ and having an average oxygen content $O_B$ of 0 to 77 atom %, preferably from 0 to 66 atom %, more preferably from 0 to 58 atom %, based on the total amount of $M_B$ and $O_B$ in the layer B, C) a layer C which comprises at least one metal $M_C$ and has an average oxygen content $O_C$, based on the total amount of $M_C$ and $O_C$ in the layer C, the average oxygen content $O_{AC}$ in layers A and C being determined in accordance with the formula (I)

$$O_{AC} = \frac{1}{2}\left(\frac{O_A}{M_A + O_A} + \frac{O_C}{M_C + O_C}\right) \quad (I)$$

and being situated within a range from 2 to 77 atom %, preferably from 4 to 66 atom %, more preferably from 25 to 58 atom %.

The object is further achieved by provision of a process for preparing a metallic effect pigment of any of claims 1 to 25, wherein the individual layers A, B, and C are arranged in succession by PVD techniques, by vapor deposition of $M_A$, $M_B$, and $M_C$, with at least layers A and C being vapor-deposited in the presence of at least one oxygen-donating oxygen source.

Preferred developments are specified in the respective subclaims.

The figures for the amounts of metal atoms M and oxygen atoms 0 relate to the number of the atoms in question. In the formula (I), therefore, the figure $M_A$ denotes the number of atoms of a metal A in the layer A, the figure $M_B$ the number of atoms of a metal in the layer B, the figure $M_C$ the number of atoms of a metal in the layer C, the figure $O_A$ the number of oxygen atoms in the layer A, the figure $O_B$ the number of oxygen atoms in the layer B, the figure $O_C$ the number of oxygen atoms in the layer C, and the figure $O_{AC}$ the number of oxygen atoms in layers A and C.

These metal atoms in layers A, B, and C may independently of one another be different or the same. For example, the metals $M_A$ and $M_C$ may be the same. In another inventive embodiment, the metals $M_A$, $M_B$, and $M_C$ are the same.

In one preferred development of the invention, the layers A, B, and C are distinguishable from one another, either in terms of the metals used or in terms of the oxygen content.

In one preferred embodiment, the metallic effect pigments of the invention have a symmetrical structure, the metals $M_A$ ad $M_C$ used or the oxygen content $O_A$ and $O_C$ each being the same, the metal $M_B$ being different from the metals $M_A$ and $M_C$, and/or the oxygen content $O_B$ being different from $O_A$ and $O_C$. In one version of the invention the metals $M_A$ and $M_C$ and also the oxygen contents $O_A$ and $O_C$ are both the same, with the metal $M_B$ being different from the metals $M_A$ and $M_C$ or $O_B$.

In accordance with another version of the invention, the metallic effect pigments of the invention may also have an asymmetric structure, it being possible for the metals $M_A$, $M_B$, and $M_C$ each to be different from one another and/or for the oxygen contents $O_A$, $O_B$, and $O_C$ each to be the same or different from one another. Alternatively, the metals $M_A$, $M_B$, and $M_C$ may each be the same or different from one another and/or the oxygen contents $O_A$, $O_B$, and $O_C$ may each be different from one another.

The present invention, in accordance with one embodiment, provides multilayer effect pigments having a central metallic core coated with at least two optically active layers A and/or C.

In accordance with one version of the invention, the amount of oxygen in layers A and C, i.e., $O_A$ and $O_C$, is higher than the oxygen content $O_B$ in the layer B.

In another version of the invention, the oxygen content $O_B$ in the layer B is greater than the amount of oxygen in layers A and C, i.e., $O_A$ and $O_C$.

In accordance with one preferred embodiment, the metallic effect pigments of the invention comprise a layer structure comprising three metallic layers A, B, and C, the amount of oxygen in layers A, B, and C being as specified above.

In accordance with the invention, the central layer B, and also the two flanking layers A and/or C, may be coated with at least one further, outer layer A' or C', respectively, the layer A' being disposed on the layer A, and the layer C' on the layer C, and the pigment of the invention thus having a five-layer structure. Layers A' and C' may be layers having at least one metal and having an oxygen content which are different from the layer A and C, respectively, although the average oxygen content is likewise situated in a range from 2 to 77 atom %, preferably from 4 to 66 atom %, more preferably from 25 to 58 atom %. All statements made above or below concerning the layers A and/or C apply corresponding to the layers A' and/or C'.

It has surprisingly emerged, however, that even with a three-layer structure of the metallic pigment, with the layers A, B, and C, a broad spectrum of color effects and flop effects can be obtained.

Described below is essentially a three-layer structure, although the process of the invention can also be used for preparing metallic effect pigments having four, five, six or seven layers, etc. Effect pigments for the purposes of the invention are platelet-like pigments, and so, in an application medium, such as a paint, ink, nail varnish, etc., they act as a multiplicity of small mirrors and are outstandingly able to adopt orientation in the application medium. The effect pigments, then, are not of spherical but rather of planar design. The light reflected from the various layers of the layer structure of the effect pigments of the invention is reflected directionally by virtue of the planar structure of the effect pigments. In order to evoke a pleasing visual impression in a viewer, it is essential that the pigments adopt an orientation approximately plane-parallel with respect to the substrate surface, so that the incident light is reflected directionally by all the pigments, i.e., is not scattered in the different directions.

Articles coated with effect pigments always have an optical impression which is dependent on the viewing angle and/or incident angle. Typical features of metallic effect pigments, in addition to the high gloss, include the lightness flop, i.e., a reduction in lightness on passing from the specular angle to steeper incident angles and/or viewing angles.

The lightness flop in the case of highly lustrous mirrorlike coatings is pronounced by a very sharp decrease in lightness in going from the specular angle to steeper incident angles and/or viewing angles.

At relatively steep viewing angles, mirrorlike coatings display a very dark appearance governed by the very smooth surfaces. Thus, for example, the strong lightness flop of a mirrorlike gold jewelry article "from gold to dark" is attributable to a very smooth surface on the jewelry article.

The invention is elucidated in more detail below by means of the detailed description, exemplary embodiments, and the reference to drawings.

DETAILED DESCRIPTION

The invention accordingly relates to the provision of multilayer metallic PVD effect pigments which comprise the following layer sequence:
A) a largely metallic layer A having a largely homogenous chemical composition, which comprises at least one metal $M_A$ and an associated average oxygen content $O_A$, based on the total amount of $M_A$ and oxygen in this layer,
B) a layer B having at least one metal $M_B$ and an associated average oxygen content $O_B$ of 0 to 77 atom %, preferably from 0 to 66 atom %, more preferably from 0 to 58 atom %, based on the total amount of $M_B$ and oxygen $O_B$ in this layer, with $M_B$ being the same or different from $M_A$,
C) a largely metallic layer C which has at least one metal $M_C$ and an associated average oxygen content $O_C$, based on the total amount of $M_C$ and oxygen $O_C$ in this layer,
the average oxygen content $O_{AC}$ being determined in accordance with the formula (I)

$$O_{AC} = \frac{1}{2}\left(\frac{O_A}{M_A + O_A} + \frac{O_C}{M_C + O_C}\right) \quad (I)$$

and being situated in a range from 2 to 77 atom %, more preferably from 4 to 66 atom %, even more preferably from 25 to 58 atom %.

Figure 1:
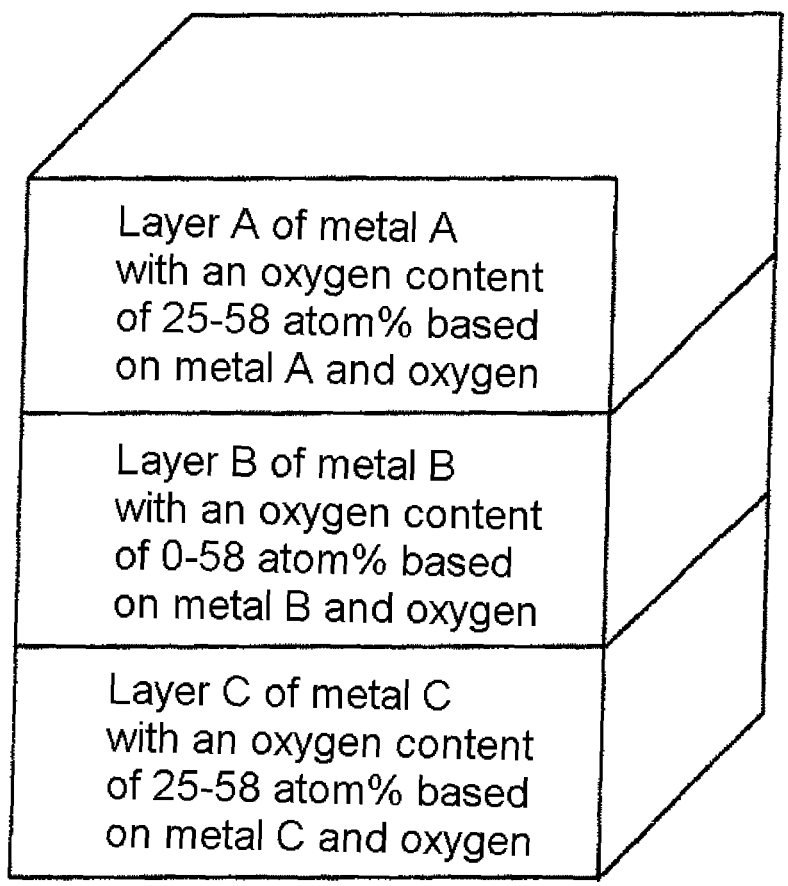
FIG. 1 shows the schematic structure of a multilayer pigment of the invention.

The layer structure of one inventive embodiment of the pigments of the invention is illustrated in more detail in FIG. 1. The amount of oxygen in layers A, B and/or C is in this case within the limits specified in claim 1. The statements below therefore apply correspondingly to higher and lower amounts of oxygen in layers A, B and/or C, as indicated in claim 1 in each case.

All of the layers are preferably each characterized in that they have a largely homogeneous, preferably homogeneous, distribution of metal atoms and oxygen atoms. Accordingly, preferably within each layer, over the layer thickness and layer width, there is no gradient of metal atoms or oxygen atoms that is measurable by the measurement methods described later on below. The high oxygen content is largely also not attributable to the formation of surface metal oxide layers which with certain metals may form spontaneously on contact with air or another oxygen source.

The metallic effect pigments provided in accordance with the invention are metallic and present a metallic effect to a viewer.

In the inventive version shown, the layers A and/or C of the pigments of the invention are designed such that, by virtue of an increased oxide content of 25 to 58 atom % oxygen, they display a more transparent appearance than pure metal layers for the same layer thickness. These layers, however, are not pure oxides, which are generally completely transparent. The same applies to an oxygen content in layers A and/or C in a range from 0 to 77 atom % or from 0 to 66 atom %.

In the prior art, in WO99/35194, pigments with a three-layer structure are described in which the inherent color of an intermediate metal layer is not altered by two external dielectric support layers.

Layers A and/or C comprise independently of one another preferably at least one metal $M_A$ and/or $M_C$ selected from the group consisting of aluminum, magnesium, chromium, silver, copper, gold, zinc, tin, manganese, iron, cobalt, nickel, titanium, tantalum, molybdenum, mixtures thereof, and alloys thereof.

Preferred metals for $M_A$ and/or $M_C$ are aluminum, silver, copper, chromium, iron or mixtures or alloys thereof. More particularly, aluminum and/or chromium have proven very suitable.

Layers A and/or C of the metallic effect pigments of the invention preferably possess a largely metallic character.

If the oxygen content $O_B$ of the layer B is higher than the oxygen content of the layers A and/or C, i.e., $O_A$ and/or $O_C$, the layer B preferably has a largely oxidic character. In this version the metallic character of the layers A and/or C may then be more strongly pronounced.

Where, in a three-layer structure of the effect pigment, the two outer layers are colorless dielectrics, they are generally not optically active. In contrast to this, the layers A and/or C of the effect pigments of the invention are optically active. Depending on the composition of the layers A and/or C, i.e., depending on the fraction of metal and oxygen in the layers A and/or C, the color impression for a viewer is changed. In the case of the metallic effect pigments of the invention, therefore, there is optical interaction between the central layer B and the outer layers A and/or C, producing the color impression to the viewer.

The high oxygen content in layers A and/or C of the metallic effect pigments of the invention is attributable to the formation of oxides and/or suboxides in addition to purely metallic fractions. As yet, however, no explanation down to the last detail has been provided as to the structural composition possessed by layers A and/or C.

Investigations with electron diffraction show two diffuse rings which are clearly distinguishable from one another and which can be assigned to metal and metal oxide in layer A and/or C. These results show that layer A and/or C contains different phases of metal and metal oxide in a very finely divided form, preferably in the nanometer range. The average size of these nanoparticles is below about 40 nm, preferably below 30 nm, more preferably 20 nm, and also, with particular preference, less than 10 nm. A layer having such structures is referred to in the context of this invention as being largely metallic.

Such finely structured phases cannot be reliably detected in SEM micrographs or by means of the abovementioned EDAX or XPS spectroscopy. Consequently, the layers A and/or C of the metallic effect pigments of the invention have a composition which is largely homogeneous in the sense of this invention. In no case, however, are layers A and/or C pure, stoichiometric oxide layers.

If the oxygen content $O_B$ of the layer B is higher than the oxygen content of the layers A and/or C, i.e., $O_A$ and/or $O_C$, layer B, correspondingly, comprises metal and metal oxide in finely divided form. The statements made above for layers A and/or C then apply accordingly to layer B.

It is now been found, entirely surprisingly, that the metallic effect pigments of the invention have innovative optical properties. Hence, in relation to a purely metallic three-layer PVD pigment with increasing oxygen content in the layers A and/or C, there is an increase in the color intensity of the effect pigments. Moreover, very high light/dark flops can be realized, the extent and color intensity of which were hitherto unobtainable with an effect pigment.

It has emerged, surprisingly, as well that the layers of the metallic effect pigments of the invention, preferably constructed homogeneously of oxygen and metal, have good weather stability and also good UV stabilities and condensation stabilities, etc.

In one preferred embodiment the two optically active layers A and C of the effect pigments of the invention together possess an average oxygen content of 30 to 57 atom % and more preferably 35 to 56 atom %. The average oxygen content is determined in accordance with the formula (I)

$$O_{AC} = \frac{1}{2}\left(\frac{O_A}{M_A + O_A} + \frac{O_C}{M_C + O_C}\right). \quad (I)$$

Below an oxygen content of 25 atom %, based on the total amount of $M_A$ and/or $M_C$ and oxygen, for example, metals with the +III oxidation state, such as aluminum or chromium, for example, deposit largely in their respective inherent color on metallic surfaces. Above 58 atom %, based on the total amount of $M_A$ and/or $M_C$ and oxygen, the metals with the +III oxidation state deposit predominantly as metal oxides, and lose their largely metallic character.

In accordance with another particularly preferred embodiment of the invention, the average oxygen content $O_A$, based on the total amount of $M_A$ and $O_A$ in the layer A, and the average oxygen content $O_C$, based on the total amount of $M_C$ and $O_C$ in the layer C, independently of one another, are each situated in a range from 25 to 58 atom %, preferably 30 to 57 atom %, and more preferably from 35 to 56 atom %.

In this embodiment, the two layers preferably both possess a largely metallic character, and the associated advantages are manifested to particularly good effect overall in the case of this effect pigment of the invention.

In order to be able to determine the oxygen content within a single layer A and/or C, it is necessary, by means of suitable focusing, to analyze in each case one single effect pigment with the methods indicated later on below. In order to determine an average value for all effect pigments, these measurements ought to be carried out on at least 5, preferably at least 10, individual pigments, and then an average value formed.

In other preferred embodiments, only one of the two layers A and/or C possesses an average oxygen content $O_{A/C}$, based on the total amount of $M_{A/C}$ and $O_{A/C}$, in the range from 0 to 58 atom %. The oxygen content of the other layer in each case may be higher or lower than this range, but the average value of the oxygen content for both layers is in the range according to the invention. Therefore one of the two layers in the case of this embodiment possesses a more metallic or more oxidic character than the other. If a layer should have an oxygen content of below 25 atom %, then the layer thickness is to be selected such that the layer is optically still partly transmissive, in order thus to be able to participate in interference phenomena.

The central layer B of the multilayer metallic effect pigment of the invention may have very different oxygen contents. The average oxygen content is 0 to 77 atom %, preferably 0 to 66 atom %, preferably 0 to 58 atom %, based on the total amount of $M_B$ and oxygen in the layer B.

In one particularly preferred embodiment, the layer B is a metallic layer having an average oxygen content of 0 to 25 atom %, preferably of 0 to 15 atom %, and more preferably of 0 to 10 atom %.

In this embodiment, the layer B possesses a metallic character. It therefore acts in general as a metallic reflector. Incident light is able, by interaction of the plane-parallel-oriented effect pigments of the invention, through the optical interaction of the layers A and/or C with the layer B, by means of interference phenomena, to lead to attractive optical impressions.

The layer thickness of the layer B in the case of metallic layers is situated preferably in a range from 10 to 200 nm, more preferably from 20 to 150 nm, more preferably still from 40 to 125 nm, and even more preferably from 50 to 100 nm.

Above a layer thickness of around 40 nm, these metallic layers are optically opaque and metallically reflecting. The optical appearance of the pigments is dictated by the interplay of the layer A and/or layer C and layer B. Below 40 nm, such layers exhibit an increasingly transparent appearance with an occasionally dark coloring. Here, the metal layer is still strongly absorbing, but is unable to exhibit the high reflectivity of a metal reflector. The optical appearance of the pigments in this case is dictated by the optical interplay of all layers A, B, and C.

Below 10 nm, the appearance of these layers is largely oxidic, since the influence of the oxide layers that form naturally on the surface of metals increases sharply, and the layer loses its metallic character.

Above 200 nm, there is no change at all in the optical properties of the layer, and thicker layers would therefore only entail unnecessarily profligate use of material.

In further inventive embodiments, the average oxygen content of the layer B is 25 to 58 atom %, preferably 30 to 57 atom %, and more preferably 35 to 56 atom %. In this case the layer B preferably possesses a largely metallic or oxidic character, and preferably has a layer thickness of 50-2000 nm.

In one preferred embodiment here the layer B, in the same way as for the layers A and/or C, possesses a largely metallic character.

In this case the layer thickness of the layer B is situated preferably in a range from 10 to 200 nm, more preferably from 20 to 150 nm, more preferably still from 40 to 125 nm, and even more preferably from 50 to 100 nm.

Layer sequences of this kind make it possible with particular preference to prepare very dark to black metallic effect pigments. This may be supported through the use of air and/or water as oxygen source (see example 13).

In another preferred embodiment, the layers A, B and/or C may be different from one another. The layers A and B are preferably different either in respect of the metal and/or in respect of the oxygen content, as stated above.

In accordance with one embodiment of the invention, it is preferred for the central layer B to be substantially oxidic and for the layers A and C that are applied to the central layer B to be substantially metallic.

In accordance with another embodiment of the invention, it is preferred for the central layer B to be substantially metallic and for the layers A and C that are applied to the central layer B to be substantially oxidic.

In another embodiment, however, the layer B may also take on a largely oxidic character. In this case it is then further preferred for both layers A and C to have a largely metallic character with in each case an average oxygen content of 25 to 58 atom %, preferably of 0 to 25 atom %, more preferably 0 to 15 atom %, and with particular preference 0 to 10 atom %. In this case the effect pigments have a Fabry-Perot structure.

In the case of largely oxidic layers, the layer thickness of the layer B may be varied from 50 to 2000 nm, preferably from 100 to 1000 nm, and more preferably from 150 to 800 nm. At low layer thicknesses, largely single-colored metallic effect pigments are obtained in this case, and, at higher layer thicknesses, effect pigments with color flops.

In contrast to the pigments known in the prior art with a similar structure, the chroma of the effect pigments of the invention is stronger. This is presumably attributable to the special properties of the outer layers A and C.

The central metallic layer B preferably comprises at least one metal selected from the group consisting of aluminum, chromium, silver, copper, gold, zinc, tin, manganese, iron, cobalt, nickel, titanium, mixtures thereof, and alloys thereof.

Preferred metals in this context are aluminum, silver, chromium or mixtures or alloys thereof.

In accordance with one preferred embodiment, the metal $M_A$ and/or $M_C$ is substantially chromium, and in the layer A and/or C, independently of one another, the average oxygen content $O_A$ or $O_C$ is situated in the range from 35 to 48 atom %, based on the respective total amount of chromium and oxygen in the layer A or C, respectively. It has been found that pigments with external chromium/chromium oxide layers as layer A and C are corrosion-stable effect pigments. If, in accordance with further embodiments, the middle layer B is silvery-reflecting (e.g., of Ag or Al in appropriate layer thicknesses), then, depending on the layer thickness of the layers A and C, a color impression is obtained which is pale gold, gold, brown, red, violet, blue, to turquoise.

In accordance with another preferred embodiment, the metal $M_A$ and/or $M_C$ is substantially aluminum and in the layer A and/or C independently of one another the average oxygen content $O_A$ or $O_C$ is situated in the range from 30 to 55 atom %, based on the respective total amount of aluminum and oxygen in the layer A or C, respectively. It has been found that pigments having external aluminum/aluminum oxide layers as layer A and C are inexpensively preparable effect pigments which, depending on the layer thickness of the layers A and C, exhibit an extraordinarily strong lightness flop. If, in accordance with further embodiments, the middle layer B is silvery-reflecting (e.g., of Ag or Al in corresponding layer thicknesses), then again, depending on the layer thickness of the layers A and C, a color impression is obtained of pale gold, gold, brown, red, violet, blue to turquoise.

The metal may be present in any layer, as for example in aforementioned layers A, B and/or C, as an alloy or mixture of different metals. In one preferred embodiment, in each layer A, B and/or C, a metal having a purity of more than 99.0% by weight is used. In this context, layers A, B and/or C may be the same or—independently of one another—different in respect of the metal used or the metals used. In that case the layers A, B and/or C may differ from one another in respect, for example, of the fraction of oxygen in atom % and/or the layer thickness. Preferably the layers A and C have a comparable, more preferably an identical, chemical composition, and with further preference the layers A and C additionally have an identical layer thickness. It is preferred, furthermore, for the chemical composition of the layer B to be different from the layers A and/or C.

The layers A, B, and C are preferably arranged in direct succession. However, there may also be one or more other layers located between the layers, such as between layer A and layer B, for example.

The optical mode of action of the layers A and/or C is dependent principally on the nature of the metal, the layer thickness, and the oxygen content. The layer thickness of the layers A and/or C independently of one another is preferably 10 to 250 nm and more preferably 40 to 150 nm.

Below a layer thickness of 10 nm, the optical effect evoked by these layers is too small, and above 250 nm the transparency is too low, thereby causing the inventive advantages of the preferably 3-layer structure to be no longer visible.

The average layer thicknesses of A and C are preferably substantially the same.

In order to generate a wide variety of optical effects, the layer thickness of the central layer B and/or the layer thickness of the layers A and/or C may be varied. For example, only the layer thickness of the central layer B of the effect pigment of the invention can be changed, in a range from 10 to 200 nm, for example, and the layer thickness of the layers A and/or C can be kept constant.

The colored metallic effect pigments of the invention preferably possess an average mean pigment thickness of 30 to 550 nm and more preferably of 50 to 300 nm.

The pigment thickness is determined critically by the layer thicknesses of the coloring layers A and/or C and by the layer thickness for B, which is situated preferably in the range from 10 to 200 nm. Above 20 nm, layer thickness B no longer has a coloring effect. Above a layer thickness of about 40 nm and an oxygen content below 15 atom %, layer B acts as an opaque metallic reflector. In this case the coloring of the metallic effect pigment is brought about only by layer A or C and layer B.

The layer thicknesses of the individual layers of the effect pigment of the invention may be determined by the skilled worker, for example, by means of SEM micrographs of transverse ground sections. In this context it is necessary to ensure that the transverse ground sections are carried out on effect pigments which are oriented substantially parallel to a defined plane. This is necessary in order to avoid measurement errors due to "tilted" pigments.

The oxygen contents of the effect pigments of the invention, determined in the context of this invention, are determined preferably by means of the ESCA method (electron spectroscopy for chemical analysis) or of Auger spectroscopy, in each case in combination with sputtering techniques. For the effect pigments it is possible here to produce a depth profile of the average elemental composition along the thickness of the pigments. Differentiation can be made between the oxygen content of the surface and that of the pigment interior. This method likewise allows particularly good representation of the layer thickness profile and oxygen profile. For an illustration of this, refer to FIG. 7.

Figure 7:
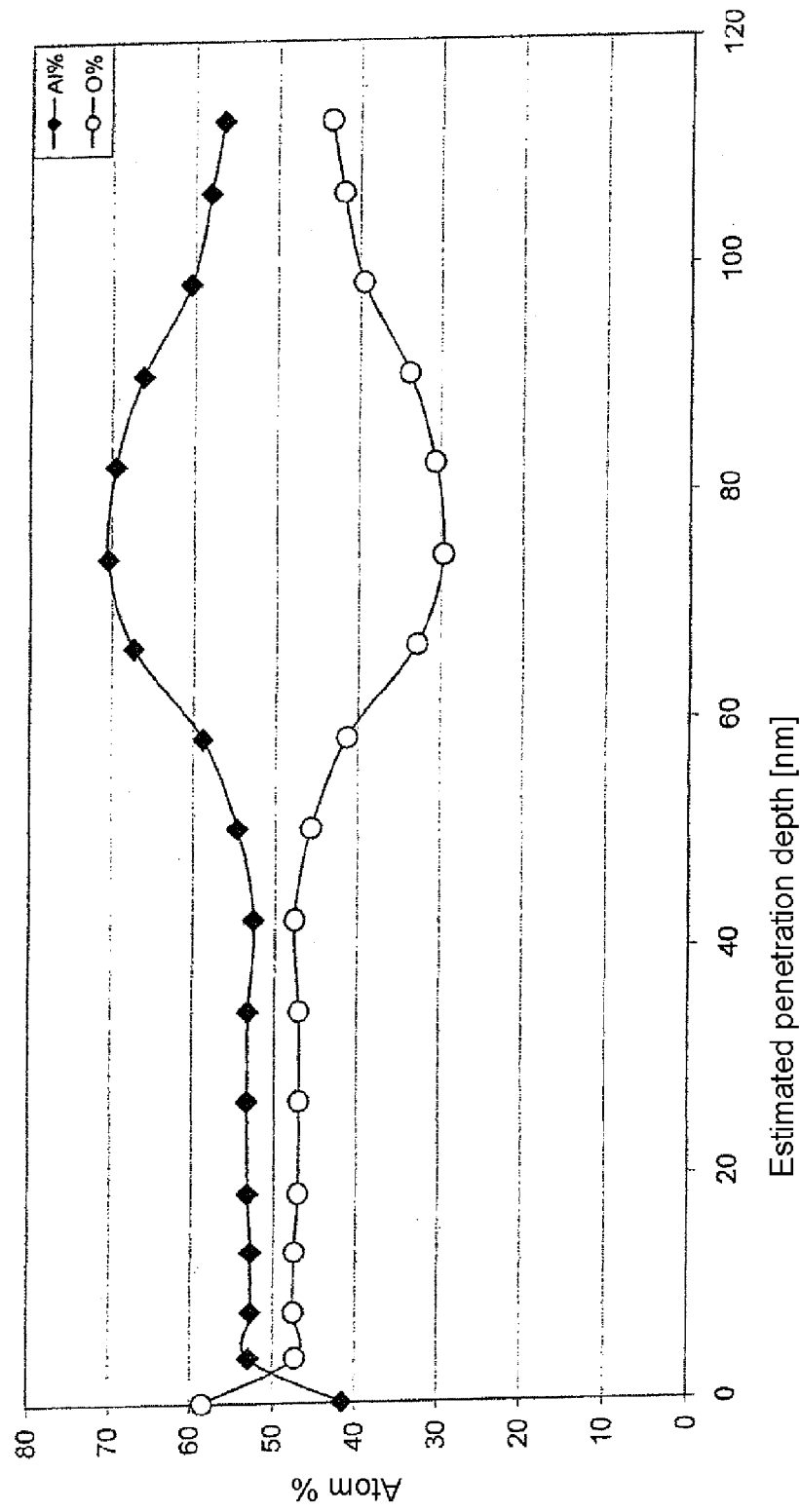
FIG. 7 represents by way of example the layer thickness profile and oxygen profile, determined by the ESCA method, for the case where the metals to be vaporized for layers A, B, and C are identical.

FIG. 7 represents the layer thickness oxygen profile of the metallic effect pigment prepared according to inventive example 9, obtained by measurement with the ESCA method and sputtering. This effect pigment is a three-layer pigment with the following layer sequence: A: oxidic Al; B: metallic Al; C: oxidic Al. Over the first approximately 50 nm of layer thickness, a constant composition is seen, with an Al fraction of 53 atom % and an oxygen fraction of 47 atom %. After a sputtering depth of approximately 50 nm, the aluminum fraction rises continuously to a maximum of 71 atom %. The oxygen fraction drops in proportion with this.

The measurement was carried out on a plurality of pigments. For this measurement, the pigment was first dispersed in acetone, and this dispersion was then applied to a glass support. Following evaporation of the solvent, the sample was analyzed. Naturally, the pigments which are oriented largely parallel to the glass substrate are present in a statistical distribution; i.e., in largely equal fractions, pigments are present in which the layer A and the layer C are pointing upward. Consequently, the oxygen content of the first measurements corresponds to an average, in accordance with formula I, of the two layers A and C. The oxygen content determined at the start of measurement is somewhat higher and is governed by the outer oxide layer which forms naturally, and is not taken into account when determining the oxygen content in the outer layers A and C. In this case, instead, the average value of the plateau that is formed is employed for the purpose of determining the oxygen content. For the layer B, the maximum metal content is to be employed for determining the metal content. This proves to be necessary since the signal of the metal content only changes slowly. The sharp broadening of this signal at the transitions from the layers A and C to the middle layer B, which per se are sharply defined interfaces, is governed by a number of factors:

a) the emergent electrons of the analyzed layer come in each case from a depth range of approximately 10 nm.
b) The measurement is carried out simultaneously on two or more pigments in each case. The measurement hence incorporates the existing layer thickness distributions of all individual layers A, B and C of all the pigments.
c) Particularly after very strong sputtering, individual pigments may have already been completely sputtered away, and underlying pigments are already being reached.

For these reasons, the maximum within a range assignable to a layer is selected for the determination of the metal content by this method.

Where a maximum plateau is established, it is employed for determining the oxygen content or metal content, respectively. Here the skilled worker is in a position to make the correct assignment. In this context it is advisable to combine the measurements of such a sputter profile with the layer-thickness analysis from SEM images. In this way the skilled worker is already informed about the layer structure to be expected. This is especially so in view of the fact that the depth scale determined by means of sputtering may carry a large error, and can then be employed only to a very restricted degree for the purpose of determining the layer thicknesses.

This method can also be implemented on individual pigments. In that case the incoming UV light is focused onto an individual pigment platelet, and measurement takes place accordingly. The pigments may be characterized beforehand by overview micrographs by means of electron emission, and the focusing controlled accordingly. In this case at least five individual pigments must be analyzed in order to obtain a representative average.

If a constant metal/oxygen composition is determined when measuring individual pigments within a layer, preferably the outer layer, then said layer in the context of this invention has a largely homogeneous composition. However, this includes any inhomogeneities which may not be determined by this measurement method.

The oxygen content of the layers can also be determined by other methods. For example, it may be ascertained by means of EDX analysis (energy dispersive X-ray analysis). In this case it is preferred to use an instrument which is integrated into an electron microscope, an example being the EDAX Genisis, Version 3.60, from EDAX.

Elucidated below is the procedure in principle for determining the elemental composition of the pigments by this method:

In the EDX analysis method, the imaging electron beam of the electron microscope, dependent on its energy and on the material, penetrates a distance into the sample surface and emits its energy to the atoms located there. Owing to the high energy of the beam electrons, electrons are ejected from the near-nucleus shells (K or L shell) of the excited atoms. This operation gives rise to x-rays by a two fold mechanism. The sharp braking of the electrons generates a continuously distributed x-radiation, the bremsstrahlung, and the refilling of the shells by external electrons, owing to associated emission events, produces a discrete x-ray spectrum. This yields the characteristic line spectrum of the atom, which allows unambiguous identification of the elements.

The x-radiation spectrum emitted by the sample under analysis is measured by means of an energy-dispersive x-ray spectrometer. The spectrum is made up of the bremsstrahlung background and a series of x-ray spectral lines. The position of the lines allows the emitting elements to be determined; the height of the lines is a measure of their relative amounts in the sample.

In EDX elemental analysis, there are a number of important boundary conditions to be observed for correct measurement of the element amounts. The samples for analysis must be:

a) homogeneous in their composition,
b) sufficiently thick for the imaging electron beam to be absorbed completely in the sample, and
c) freely accessible to the electron beam, without disruptive effects of a matrix and/or a background.

The higher the atomic number of the elements, the stronger the bonding of the near-nucleus electrons. Consequently, the ionization energy required increases in line with the atomic number. The kinetic energy of the electron beam must be adapted to the elements to be analyzed. The depth of penetration of the electron beam into the material under analysis, however, is dependent on its energy. The electron beam penetrates the sample in an intensity distribution which has a pear-shaped structure and is also referred to as a pear-shaped excitation cloud. When thin layers are being analyzed, it must be borne in mind that they can be easily punctured by high-energy electrons. If thin layers, i.e., layers in a range of below 250 nm, are to be measured, the kinetic energy must not be more than a few keV. Correspondingly, in the case of heavier elements, the excitation of the higher shells must be implemented instead. The analysis must then be made via the evaluation of the L or M lines of the elements.

Specifically, the procedure for analyzing thin-layer, platelet-shaped pigments is as follows:
Prior to the analysis, the EDX measuring unit is calibrated using suitable, commercially available standards in accordance with manufacturer data.

By means of electron-microscopy imaging, the layer thickness of the layer under investigation must be determined. Elemental analysis at a relatively high voltage of approximately 10 to 20 kV provides information of all of the elements present in the sample under analysis, and also of further elements located in the underlying substrate. On the basis of the thickness and the elemental composition of the layer, a Monte Carlo simulation (preferably: Program: EDAX Flight-E, Version 3.1-E) is used to determine the electron energy at which the layer volume is fully filled, but still not punctured, by the penetrating electron beam. In this case the pear-shaped excitation cloud has the greatest volume.

In the next step it is necessary to determine whether and, if so, which x-ray lines are excited for this radiation energy. It may be necessary to fine-tune the kinetic excitation energy somewhat to the spectral lines.

A first sample measurement with the parameters thus determined should be carried out and analyzed. If x-ray lines of substrate elements are seen in the spectrum, then the radiation energy setting is too high and must be corrected.

Then, a number of measurements are carried out on the layer, with the radiation voltage increasing in steps, and are evaluated. There should be only minor fluctuations in the element amounts found. If the fraction of light elements in the analysis begins to show a marked fall as the voltage increases, the radiation energy is too high and must be reduced.

With the optimum parameters thus determined, measurements are carried out at two or more points in the layer, and the element amounts are determined. The results must be examined for plausibility, and the scattering of the measurements ought not to amount to more than about 5%.

Figure 2:
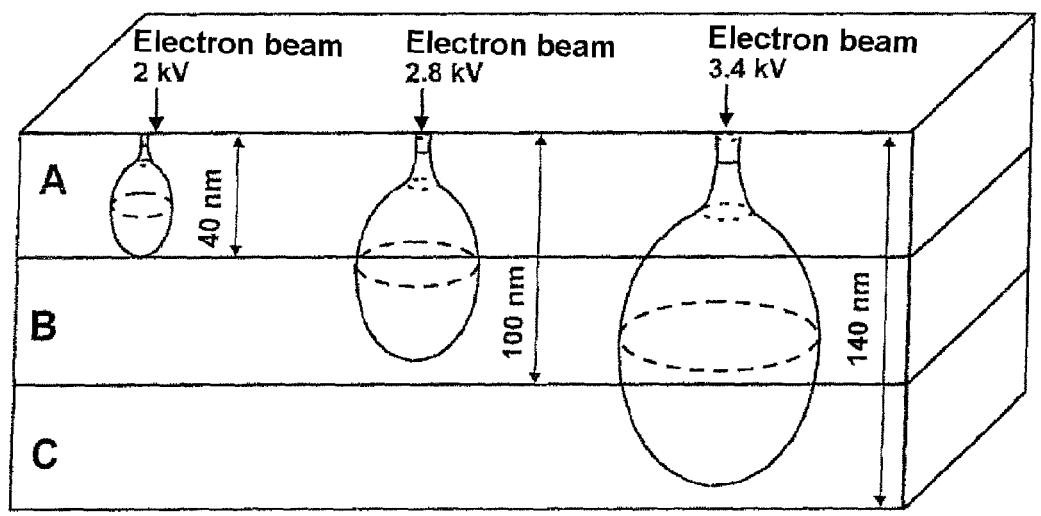
FIG. 2 provides a schematic outline of the depth effect in the EDX method. Here, irradiated x-rays cause electrons to be ejected from the K or L shell of the elements of the measurement sample. These electrons, however, possess only a certain range. The figure outlines the throw of the electron beam (the pear-shaped excitation cloud) into the three-layer pigment of the invention. Corresponding to the respective depths of penetration, it is possible to determine the atomic oxygen content, based on the total amount of oxygen and of the metal vapor-deposited for coating, in atom %.

In order to be able to analyze the layer thickness/oxygen profile on the entire layer sequence of the pigments of the invention, the depth of penetration into the layer of the pigment can be achieved by increasing the excitation energy of the electron beam (the "pear-shaped excitation cloud") in steps, as shown schematically in FIG. 2. In this case the depth of penetration of the electron beam is predetermined in each case, and the related oxide content is ascertained.

Figure 6:
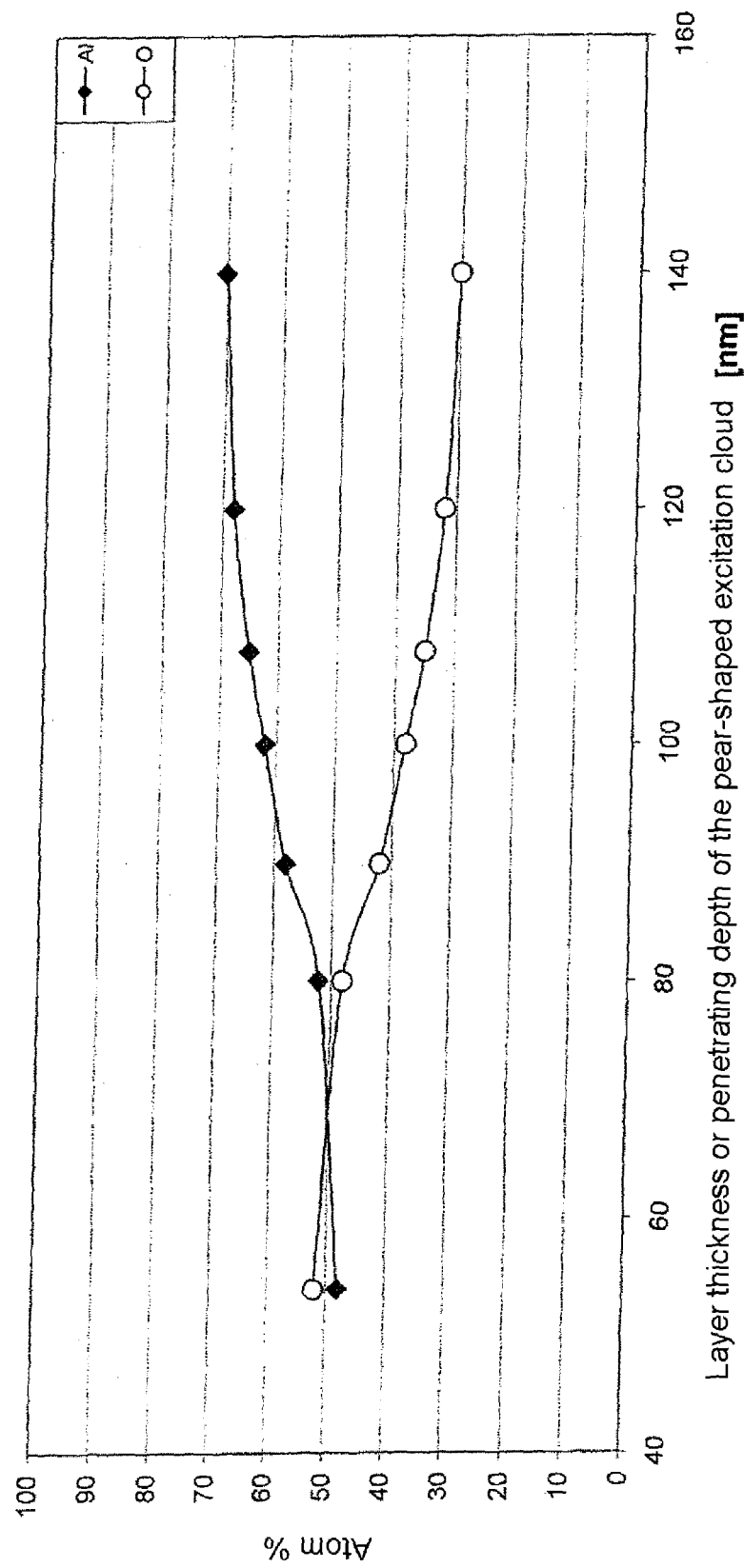
FIG. 6 shows the characteristic profile of the oxygen content as a function of layer thickness, determined via EDX methodology.

In this way it is also possible to include the lower-lying layers in the analysis of the oxygen content or metal content. FIG. 6 shows the layer thickness profile and oxygen profile obtained with this method on effect pigments prepared in accordance with inventive example 10.

This method can be employed to very good effect to determine the oxygen content in layers A and/or C. It is difficult, however, to analyze the middle layer B, since in this case the signal always includes the topmost layer as well. Accordingly, in accordance with the intensity profile of the pear-shaped excitation cloud of the electron beam, folded values of the first two layers are obtained.

The analysis of individual layers can be carried out, however, if this method is combined likewise with sputtering techniques. In this case, as described above, the excitation energy of the electron beam must be optimized for each individual layer.

It is also possible to carry out individual analysis of pigments by appropriately focusing the exciting electron beam onto those individual pigments. In this way the composition of layers A and C can be analyzed. In this case it likewise necessary to analyze at least five individual pigments, in order to obtain a representative average.

The three-layer structure with the outer layers with a high oxygen content has the effect that, in terms of their mechanical properties, overall, the metallic effect pigments of the invention tend to have a brittle behavior, comparable with oxides or glasses.

In comparison to the known PVD metallic pigments, therefore, they possess performance advantages. Conventional PVD metallic pigments have a tendency, on account of their thinness and the ductility of the metal, to roll up. Because of their flexibility it is true that they have the capacity to "conform" outstandingly to a substrate, yet in an application, after curing of the binder, there may always be a small fraction of the pigments that is deformed, and in the extreme case even "rolled up". This phenomenon is accompanied by losses in optical quality. The capacity to roll up is disruptive in particular in the operation of preparing the pigments, after detachment from the film. Following the subsequent comminution of the pigments, it is true that fewer pigments are rolled up, and yet the effect is still partly present and may cause disruption later at the application stage. Moreover, these pigments are mechanically unstable, as manifested, for example, in a sensitivity to the action of strong shearing forces.

WO 99/35194 describes metallic PVD pigments which in order to improve their mechanical properties carry support layers of a dielectric, such as $SiO_2$, for example, on both sides. The dielectric layers are applied to the metal layer likewise by PVD techniques. This, however, is a very laborious technique, the economics suffering particularly from the fact that metal oxides possess substantially slower vaporization rates than metals.

With the colored metallic effect pigments of the invention, the desired mechanical stiffness is realized through the multilayer structure and also through the—in one inventive embodiment—high oxygen content of the outer layers A and C. The comminuted pigments do not roll up, and exhibit a very homogeneous appearance, with smooth surfaces without waves or bulges, along their longitudinal extent. The effect of the high oxygen content of the layers A and C and also, optionally, B as well, in terms of mechanical properties, is to bring about a largely glasslike or ceramiclike stiffness of these layers. Accordingly these pigments can be comminuted outstandingly after detachment from the film. The resulting effect pigments have very smooth fracture edges. This has advantageous consequences for the optical properties of the pigments, since the smooth fracture edges mean that there are fewer scattering centers for the incident light.

The effect pigments of the invention are always platelet-shaped. Their longitudinal extent, expressed by the $D_{50}$ value of the cumulative undersize distribution, is situated in the typical ranges from 2 to 250 µm, preferably from 5 to 150 µm, and more preferably from 7 to 50 µm. The size distribution is measured typically by laser diffraction methods.

The metallic effect pigments of the invention have form factors of 4 to 8500, preferably of up to 10 to 5000, and more preferably of 20 to 1700. The form factor is defined as the ratio of the $d_{50}$ value of the cumulative undersize curve of the size distribution to the average thickness of the platelet-shaped pigments.

The effect pigments of the invention have, surprisingly, an extraordinarily high color saturation, or strong chroma, and in many embodiments a strong lightness flop. This can be determined from applicator drawdowns. The applicator drawdowns are carried out in preferably conventional varnish systems, i.e., water-free varnish systems, without addition of other effect pigments and/or color pigments or matting agents. Particular preference is given to using nitrocellulose varnishes, such as the commercially available nitrocellulose varnish Dr. Renger Erco Bronzemischlack 2615e, from Morton, for example. The concentration of the effect pigment ought to be high enough to obtain a hiding applicator drawdown, and is dependent on the nature of the metal, the metal content, and the film thickness (see also table 5).

Furthermore, the pigments in accordance with the inventive examples, and in particular the gold-colored pigments, exhibit a very strong lightness flop, by virtue of the oxidic integration into the outer layers.

The lightness flop is specified by DuPont in accordance with the following formula (II) (A. B. J. Rodriguez, JOCCA, (1992(4)) pp. 150-153):

$$\text{Flop index} = 2.69 \times \frac{(L_{15°}^* - L_{110°}^*)^{1.11}}{(L_{45°}^*)^{0.86}} \quad \text{(II)}$$

The flop values or flop indices of the effect pigments of the invention are in the range from 30 to 70, preferably 35 to 65, and more preferably 40 to 60.

At close to the specular angle, the effect pigments of the invention appear still relatively light, comparable with aluminum pigments prepared by conventional milling methods. At steeper viewing angles, however, the lightness values drop off very quickly, and at 45° have already reached values extending close to black coatings. This gives them such extraordinarily high flop indices.

In contrast, highly illustrious aluminum pigments obtained by PVD processes, which to date have represented the effect pigments having the greatest brilliance, are known in corresponding applications to have flop indices in the range from 20 to about 30.

Accordingly the flop indices of the effect pigments of the invention are generally significantly higher, but in some cases overlap, with those of pigments known from the prior art. As a parameter for the further characterization of the optical properties of the pigments of the invention, the lightnesses $L_{45°}^*$ are employed. The $L_{45°}^*$ values of the effect pigments of the invention are in the range from 1 to 25, preferably from 1.4 to 20, and more preferably from 1.7 to 12 lightness units. These very low values are evidence of the strong flop to dark. Known metallic PVD pigments possess $L_{45°}^*$ values of more than 35.

Furthermore, the metallic effect pigments of the invention possess a high color saturation, which in colorimetric terms is reflected in a chroma value. The chroma, measured at a differential angle of 15°, is more than 20, preferably more than 30, and more preferably more than 40 units.

In one particularly preferred embodiment the metal $M_A$ of the layer A and the metal $M_C$ of the layer C are of the same kind. Pigments of this kind are particularly simple to prepare, as will be elucidated in more detail below.

In a further-preferred embodiment, the metals $M_A$ of the layer A, $M_B$ of the layer B, and $M_C$ of the layer C are of the same kind.

Moreover, it is preferred for the average layer thicknesses of the layers A and C to be substantially the same. The reference here is to deviations in the average layer thicknesses of A and C of up to 10%. Where these layers possess an approximately equal layer thickness and, moreover, are of the same kind, the metallic effect pigments are pigments with a symmetrical construction. In an application, these pigments produce particularly clean and distinct color effects. Metallic effect pigments having a symmetrical construction are preferred in accordance with the invention.

Described below are other preferred embodiments of the invention.

Exemplary Embodiment A

Structure: Oxidic Cr/Ag/Oxidic Cr or Oxidic Cr/Al/Oxidic Cr

In these preferred embodiments the colored metallic effect pigment is characterized in that the metal $M_A$ and/or $M_C$ is composed substantially of chromium and possesses an average oxygen content of 35 to 48 atom %, based on the total amount of chromium and oxygen. In these embodiments the metal $M_B$ is composed preferably of aluminum and/or silver.

In both cases it is possible to produce extremely attractive gold-colored metallic effect pigments by adjusting the layer thickness of the oxidic Cr layers. In a layer thickness range of 10 nm-35 nm for the oxidic Cr layers, gold hues from pale gold (layer B: aluminum) or silver beige (layer B: silver) through to very intense reddish gold are produced. It is also possible, for example, to achieve the hue of true gold. Preferably, where silver or Al is used as layer B, layer thicknesses in a range of 50-100 nm, and more preferably of 15-40 nm, are employed.

Exemplary Embodiment B

Structure: Oxidic Al/Ag/Oxidic Al or Oxidic Al/Al/Oxidic Al

In the case of this preferred embodiment the colored metallic effect pigment is characterized in that the metal $M_A$ and/or $M_C$ is composed substantially of aluminum and possesses an average oxygen content of 30 to 55 atom %, based on the total amount of aluminum and oxygen. The metal $M_B$ in the case of these embodiments is composed preferably of aluminum or silver.

Another preferred embodiment of the colored metallic effect pigments in this case is given by the layer sequence of oxidic Al/Al/oxidic Al, a feature of which is that the metal $M_A$ is identical to metal $M_B$ and identical to metal $M_C$.

The mode of action of the outer oxidic aluminum layers is similar to that of the oxidic Cr layers in above-described variant A. The hues that are achievable are the same.

In a layer thickness range of 10 nm-60 nm for the oxidic Al layers, gold hues from pale gold (layer B: aluminum) or silver beige (layer B: silver) through to very intense reddish gold are produced.

The intermediate metallic layer B in the two above-described variants A and B has in each case a metal content of 70 to 100 atom %, based on the amount of metal and oxygen in the layer B, with it being possible for $M_B$ to be the same as or different from $M_A$.

In the preferred embodiments the metal $M_B$ used in the layer B is aluminum and/or silver, the oxygen content being preferably in a range from 30 to 0 atom %, more preferably from less than 25 to 0 atom %, even more preferably from less than 20 to 0 atom %, even more preferably still from less than 10 to 0 atom %, based in each case on the metal content and oxygen content of the layer B.

The metal content of the layer B is, for aluminum and/or silver, preferably 70-100 atom %, based on the aluminum or on the silver, respectively, and on any oxygen present in the layer B. Below the stated metal content for silver or else aluminum, the central layer B may be too transparent in its effect. Where silver and/or aluminum are used in layer B, it is preferred to employ a layer thickness in the range of 50-100 nm, more preferably of 20-40 nm.

In order to stabilize the effect pigments of the invention, especially for use in waterborne coatings or aqueous printing inks, they may optionally be coated, preferably envelopingly, with an anticorrosion coat.

Here it is possible to employ the customary methods, such as treatment with organically modified phosphoric acids and/or phosphonic acids and/or derivatives thereof. Where the outer layers A and C are composed of aluminum, chrominating may be carried out along the lines of the method disclosed in EP 0 259 592 B1. Moreover, treatment of the pigment surfaces may be carried out with vanadium compounds and/or molybdenum compounds, and also a combination of these techniques. Furthermore, the pigments of the invention may also be coated with polymers or metal oxides. The metal oxides comprise preferably $SiO_2$, boron oxides, aluminum oxides, molybdates, and vanadates, and include their hydroxides and oxide hydrates or mixtures thereof.

In one particularly preferred embodiment, the preferably enveloping anticorrosion coat comprises $SiO_2$ or consists of $SiO_2$. With particular preference the $SiO_2$ layer is applied envelopingly to the effect pigment by sol-gel methods.

In other preferred embodiments, the effect pigments of the invention protected with a corrosion coat against corrosion may also, additionally, have organic-chemical surface modifications, such as silanes, titanates or aluminates, for example. The organic-chemical surface modifications may have the effect of compatibilization with the surrounding application medium, such as the binder system of a paint or an ink, for example. An organic-chemical aftercoating of this kind may, for example, permit chemical attachment to binder of paints or inks, thereby allowing covalent attachment of the effect pigments of the invention. Covalent attachment of the effect pigments to the binder system increases the condensation resistance and mechanical stability of the coating medium, of inks and paints, for example, after curing.

Described below are various processes for providing the effect pigments of the invention.

The process used to prepare the effect pigments of the invention is always a PVD process, i.e., the individual layers, in the case of a three-layer system the layers A, B, and C, are applied by PVD techniques in succession and preferably to one another.

A process for preparing the metallic effect pigments of the invention preferably comprises the following steps:

a) coating a preferably mobile substrate in a vacuum chamber by physical vapor deposition (PVD) with at least one metal $M_A$ in the presence of oxygen, to form the layer A on the substrate, b) coating the layer A in a vacuum chamber by means of physical vapor deposition (PVD) with at least one metal $M_B$ in the presence or absence of oxygen, to form the layer B, c) coating the layer B in a vacuum chamber by means of physical vapor deposition (PVD) with at least one metal $M_C$ in the presence of oxygen, to form the layer C, d) detaching the metallic layer stack from the substrate, e) comminuting the metallic layer stack to give metallic effect pigments, f) optionally converting the metallic effect pigments into a dispersion or paste.

The dispersion is preferably likewise present in an organic solvent. In one variant the fraction of organic solvent in the dispersion is at least 70% by weight.

The effect pigments of the invention may alternatively be present in a more concentrated form, such as a paste, for example. In that case the solvent content is up to 60% by weight, preferably up to 50% by weight, based on the metallic effect pigment paste.

The metallic effect pigments of the invention may also be present in a compacted form, as pellets, granules, tablets, sausages, briquettes, etc., the solvent content being preferably less than 10% by weight, more preferably between 3% and 8% by weight, based in each case on the weight of the compacted form.

Vapor deposition with metal may take place by known techniques such as, for example, electron beam technology or methods with resistance heating or radiation heating. In these known techniques, the metals are disposed in appropriate vaporizers and are vaporized from them, the metal vapor depositing on a moving or stationary substrate.

The thickness of the external metal layers A and/or C may be checked by transmittance measurements during application. Owing to the partly oxidic character of the film layer, the transmittances are lower than in the case of the vaporization of pure metals. The checking of the layer thickness of the central layer B may take place, for example, via on-line layer resistance measurements.

If an alloy is used rather than a metal M, then that alloy is produced either from separate vaporizers, by flash vaporization, jumping beam vaporizers, or the like, for example, by simultaneous condensation of the metals or by means of suitable vaporization methods, such as, for example, sputtering or electron beam technology.

The moving substrate may consist of polymer films, such as polyterephthalate, for example, or of a metal strip, which is preferably a revolving metal strip.

The oxygen in the vapor deposition step may be provided through a multiplicity of possible process variants.

These variants may comprise the provision of molecular oxygen from atmospheric oxygen or else the controlled metering of oxygen gas into the vacuum chamber. In the latter case, the term reactive PVD might be used.

Preferably, pure oxygen is supplied to the vacuum chamber, since relatively fine metallic phases or relatively fine metal oxide phases are formed, as a result of which the perceived color of the metallic effect pigments can be controlled with greater precision.

Another suitable oxygen source is water which is still present in the vacuum chamber or is introduced specifically. This water may be of atmospheric origin or may come from a water store. Water stores that are suitable include hydrate compounds, for example. The hydrate compound must itself be of sufficiently low volatility in order not to sublime under the vacuums that are present. Advantageously, however, the hydrate compound gives off water, where appropriate on supply of heat. Moreover, water vapor may be metered controlledly into the vacuum chamber in the course of vapor deposition.

It should be noted here that, under the low pressures of a vacuum coating chamber, water is present in solid form. The water must therefore be sublimed by means of a suitable heat source. This heat source may be situated, for example, in the vaporizer sources in the case of a resistance-heated metal vaporization process, producing a not inconsiderable heat.

Furthermore, oxygen may come from the preferably moving substrate, a moving film, for example, to which first a release coat and subsequently the metal is applied by vapor deposition. The oxygen can of course also be provided by any desired combination of these process options.

The vacuum pressure in the case of step a) is preferably relatively high. Preferably the vacuum pressure is $2 \times 10^{-4}$ to $1 \times 10^{-1}$ mbar, more preferably $3 \times 10^{-4}$ to $1 \times 10^{-2}$ mbar, and, more preferably still, $4 \times 10^{-4}$ to $3 \times 10^{-3}$ mbar. Dark layers are obtained preferably at higher pressures.

In PVD processes for preparing metallic pigments it is conventional to set pressures of $1 \times 10^{-4}$ mbar or less. Moreover, no oxygen-donating donor sources are arranged in the vacuum chamber or introduced into it.

In one preferred process, the coating is applied by means of vaporization sources connected in series.

This process variant for preparing the metallic effect pigments of the invention comprises the following steps:
a) coating a preferably mobile substrate, preferably a circulating or moving belt, in a vacuum chamber with at least the metal $M_A$ from a vaporizer source $VQ_A$ in the presence of an oxygen-donating oxygen source, to form the layer A,
b) coating the layer A on the preferably mobile substrate, preferably a circulating or moving belt, in a vacuum chamber with at least the metal $M_B$ from a vaporizer source $VQ_B$ in the presence or absence of an oxygen source, to form the layer B,
c) coating the layer B on the preferably mobile substrate, preferably a circulating or moving belt, in a vacuum chamber with at least the metal $M_C$ from a vaporizer source $VQ_C$ in the presence of an oxygen source, to form the layer C,
d) detaching the metallic layer stack from the preferably mobile substrate, preferably a circulating or moving belt,
e) comminuting the metallic layer stack to form metallic effect pigments,
f) optionally converting the metallic effect pigments into a dispersion or paste.

In accordance with one preferred development of the process of the invention, the individual vaporizer sources $VQ_A$, $VQ_B$, and $VQ_C$ are separate from one another or separate in each case in pairs from one another.

Figure 4A:
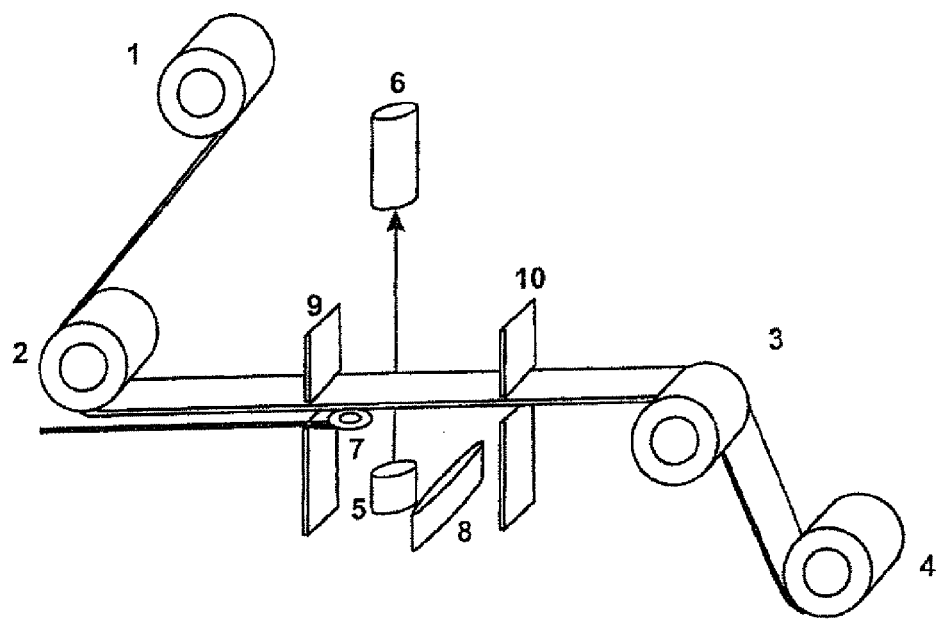
FIG. 4a shows the schematic representative of a belt unit with a vaporization source which is arranged in the vacuum chamber of FIG. 3 (without rotating-plate device).
Figure 4B:
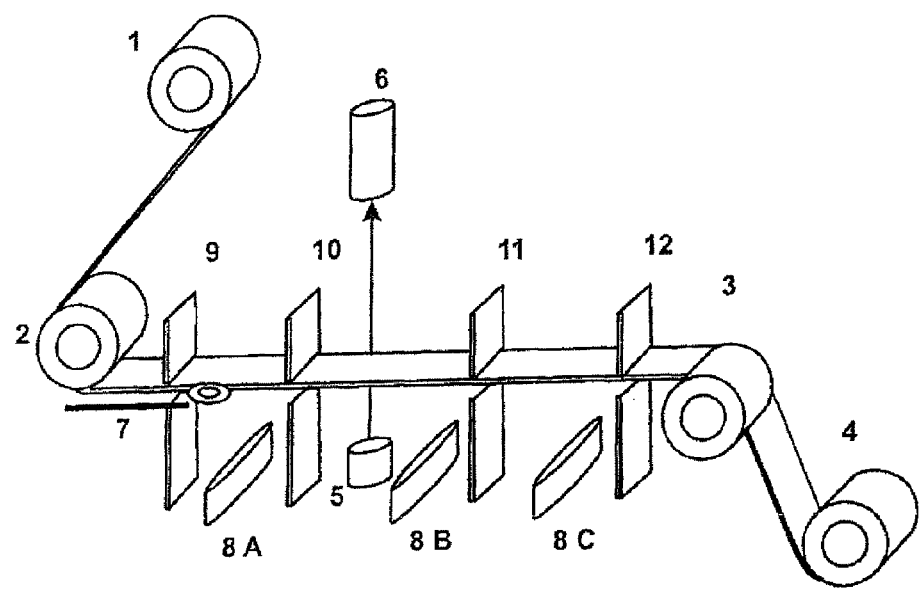
FIG. 4b shows the schematic representation of a belt unit in the coating of a striplike substrate with three vaporization sources.

Optionally the process for preparing a metallic effect pigment may be modified further, as shown by way of example in FIG. 4b, by separating the individual vaporizer sources 8A, 8B, and 8C from one another, for the vaporization of the metals, by separating means such as shutters or walls. FIG. 4b shows the diagrammatic representation in the case of the coating of a strip-like substrate via three vaporizer sources 8A, 8B, and 8C. In this case the moving substrate provided with a release coat, such as a film provided with release coat, for example, is passed from the source roll 1 over the deflection rolls 2 and 3 to the roll take-up device 4. The arrangement is arranged within a vacuum chamber (not shown). Arranged below the moving substrate are the vaporizer sources 8A, 8B, and 8C, from which the metal or the metals are vaporized in the direction of the moving substrate. In this embodiment the vacuum chamber is subdivided by partition walls 9-12. In this case the oxygen-donating oxygen sources may be arranged at a distance, for example, from the vaporizer sources 8A within the partition walls 9 and 10, and from 8C within the partition walls 11 and 12. If desired, it is also possible to arrange oxygen sources at a distance from the vaporizer source 8B. In this case, the distance of the oxygen sources from the respective vaporizer and from the moving substrate is an important parameter.

It is, of course, also possible to provide feed ports in the vacuum chamber via which oxygen-containing compounds, such as oxygen or water, for example, are supplied. The oscillating quartz measuring device 7 allows the evaporation rate to be monitored, and the transmittance measuring device allows the layer thickness of the vapor-applied film to be checked.

The process depicted in FIG. 4b is continuous; the moving substrate, preferably a strip film provided with a release coat, is passed at constant speed through the vacuum chamber. The layer thicknesses of the layers A, B, and C can be adjusted here through the vaporization rate and/or through the distance of the vaporization source from the moving substrate.

The layers A and C required for the colored metallic effect pigments may be realized, for example, by means of a greater distance of the vaporizer sources 8A and 8C from the moving substrate, revolving or moving belt, for example, optionally in combination with the selected shutter arrangement, in order to obtain lower layer thicknesses. It is also possible to provide individual settings for the heating powers and hence for the vaporous depletion and vapor deposition rate of the vaporizer sources.

In order to generate the metallic layer B it is then possible, preferably, to make the distance from the vaporizer source 8B lower than is the case with the vaporizer sources 8A and 8C, in order to generate as high as possible a metal density or layer thickness. Likewise, a higher layer thickness for the metallic layer B can be obtained if the heating power is increased, or the vaporous depletion rate intensified, for the vaporizer source 8B.

The great advantage of this particularly preferred process variant is that the complete layer sequence of the pigment of the invention is applied in a single coating operation.

Figure 9:
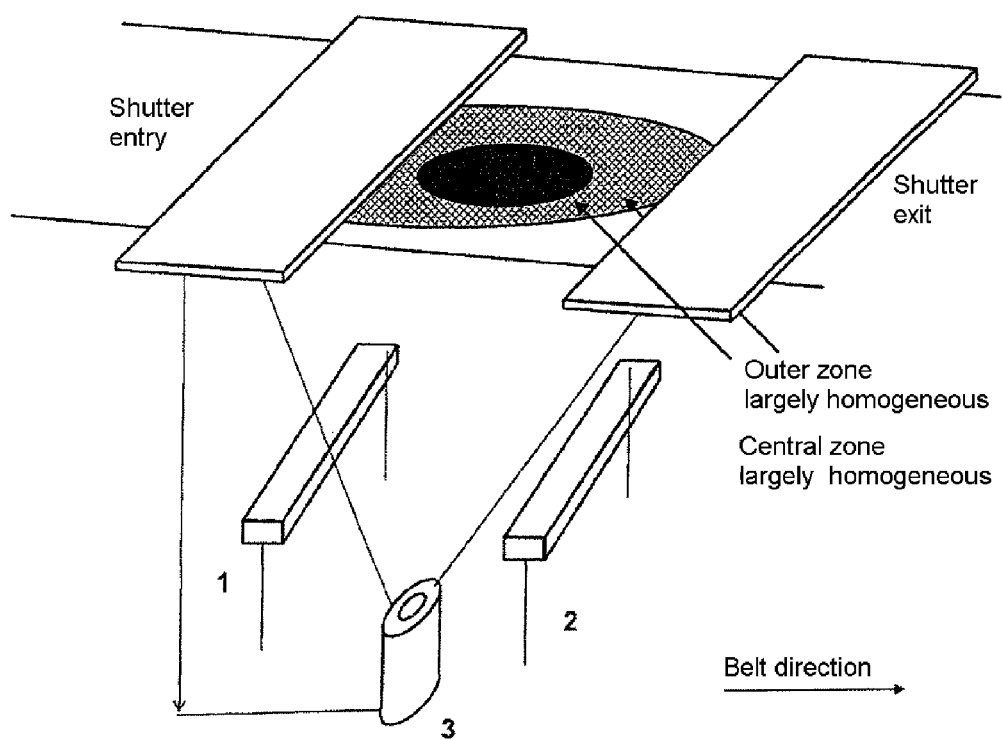
FIG. 9 shows schematically the diagram of the base area of a striplike substrate and the intensity distribution of a vaporizer cone on this striplike substrate, with two regions of concentration; in this example, the region having the highest concentration of metal atoms and the lowest concentration of oxygen atoms is located in the center and is shown in black. This inner region is surrounded by an outer region, shown with crosshatching, in which the concentration of metal atoms is lower and the concentration of oxygen atoms higher than in the inner region. The relative extent of these two regions to one another can be influenced by the arrangement of the oxygen-donating oxygen source to the side of the metal vaporizer source.

A further preferred process variant is characterized in that $M_A$, $M_B$, and $M_C$ are identical, identical in pairs or different from one another, and, from a metal vaporizing source or two or more metal vaporizing sources, a mobile substrate, preferably a rotating or moving belt, is coated with metal in a vacuum chamber in the presence of one or more oxygen-donating oxygen sources, accompanied by formation, between the metal vaporizing source, the oxygen source, and the mobile substrate, of three-dimensional concentration regions of metal vapor and oxygen in the vacuum chamber, as a result of which, by physical vapor deposition, the at least three layers A, B, and C are deposited on the mobile substrate in succession with metal contents and oxygen contents that are distinguishable from one another (see FIG. 9).

This further preferred process variant exploits the fact that, in the vaporization of metals, starting from a vaporizer source, approximately concentric circles with different concentrations of metal can each be deposited on a nonmoving substrate. These different metal concentrations vapor-deposited on the substrate are attributable to the fact that, in the space between vaporizer source and substrate, the different path lengths mean that the metal atoms given off from the vaporizer source form three-dimensional concentration ranges in the form of vaporization cones.

FIG. 9 shows, schematically, a region with high metal concentration, in the form of a circular area shown in black, and a region concentrically surrounding that region, with a lower metal concentration, in the form of an annular area shown with square crosshatching. This concentric concentration profile is obtained when a stationary substrate is vapor-coated with metal from a vaporizer source arranged beneath the substrate.

In accordance with one preferred process variant, in that one cover device, such as a shutter, or two or more cover devices, such as shutters, for example, are arranged between metal vaporization source, oxygen source, and mobile substrate, said device or devices suppressing the possible formation of transition layers between the layers A, B, and C, with the consequence that the at least three successive layers A, B, and C can deposit each with mutually distinguishable metal and oxygen contents.

Figure 10:
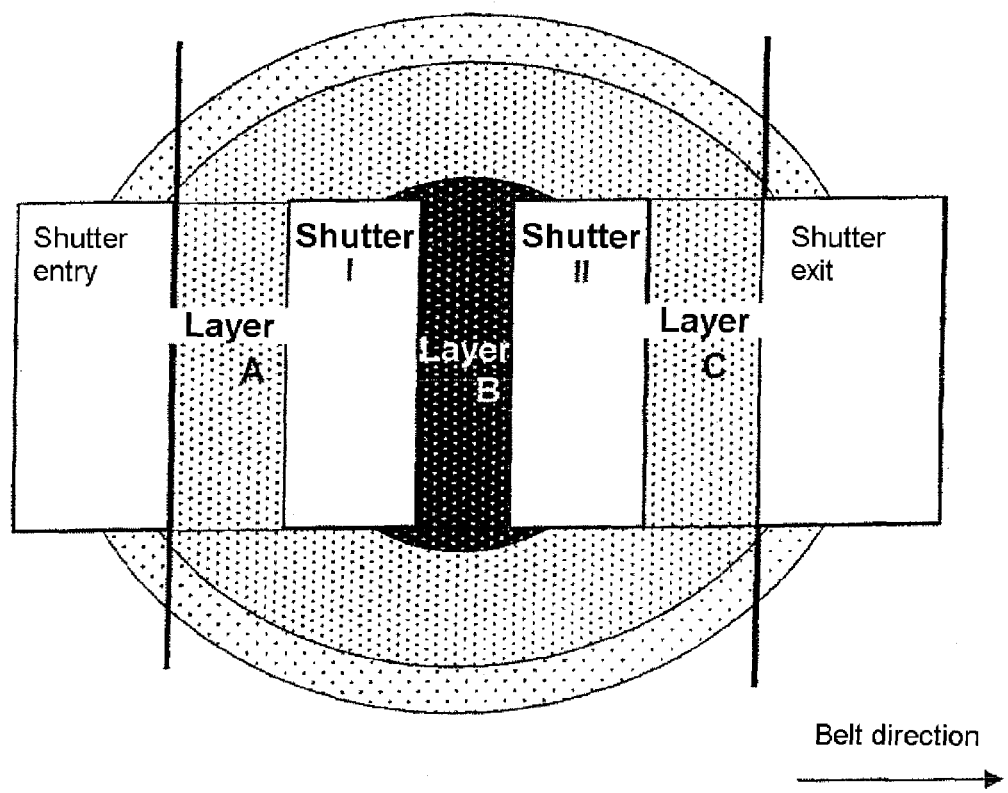
FIG. 10 shows how, starting from the intensity distribution depicted in FIG. 9, it is possible, by arrangement of masking devices, such as the shutters I and II that are shown, above the belt which is moving in the direction shown, to apply layers with defined and largely homogeneous levels of metal atoms and oxygen atoms one above another to the belt. In this exemplary version, for the resultant layer structure with three layers A, B, and C, layers A and C have the same composition and are largely oxidic. Layer B is largely metallic.

By arranging cover devices, such as shutters, for example, it is possible to separate more concentrated metal regions from less concentrated metal regions. FIG. 10 shows one exemplary arrangement of cover devices in the form of shutters, thus separating defined regions of low metal concentration, characterized as layer A, from a region with high metal concentration, identified as layer B, and in turn from a region with low metal concentration, identified as layer C, on the substrate from one another.

In the case of a moving substrate, such as a strip film, for example, which is guided from the shutter entry I to the shutter exit II (see FIG. 10), first layer A, then, above it, layer B, and finally, atop it, layer C are applied in a continuous process. The shutters I and II shut out the transition concentrations, and so the layers A, B, and C have sharp transitions.

In accordance with another preferred process variant, the at least one oxygen source is disposed in the form of water, water-donating substances, oxygen-donating substances and/or oxygen gas in the vacuum chamber, or the vacuum chamber has one or more feed ports for oxygen or oxygen-donating substances, such as water or water vapor, for example.

It is preferred for there to be a controlled metered addition of oxygen gas in the vacuum chamber during the formation of the layers A and/or C and optionally during layer B.

Depending on the desired composition of the respective layer, the oxygen source should be positioned at a defined distance from the moving substrate and from the respective vaporizer source.

Into the marginal regions of the vaporization cone (see FIG. 9) it is possible for oxygen-containing compounds, such as oxygen or water, to be introduced, and so, in the layers A and C, the desired fraction of oxygen is realized. Depending on the location at which the oxygen-containing compound is added, the layer B may likewise comprise oxygen in different, defined amounts. If an oxygen source is positioned very close to the vaporizer source, then the layer B may also be made almost entirely oxidic.

Oxygen is present, even at a very low pressure, as a residual gas in the form of water in the vacuum chamber. When a metal is vaporized, the outer regions of the vaporization cone (FIG. 9), already diluted with oxygen, may have air metered into them controlledly, with the consequence that these vaporization regions with already relatively low metal concentration are additionally enriched with oxygen. In this case the central layer B does not lose its metallic reflector capacity provided that care is taken in the process to ensure that only the outer regions of the vaporization cone are "diluted" with oxygen within the specified limits.

Figure 15:
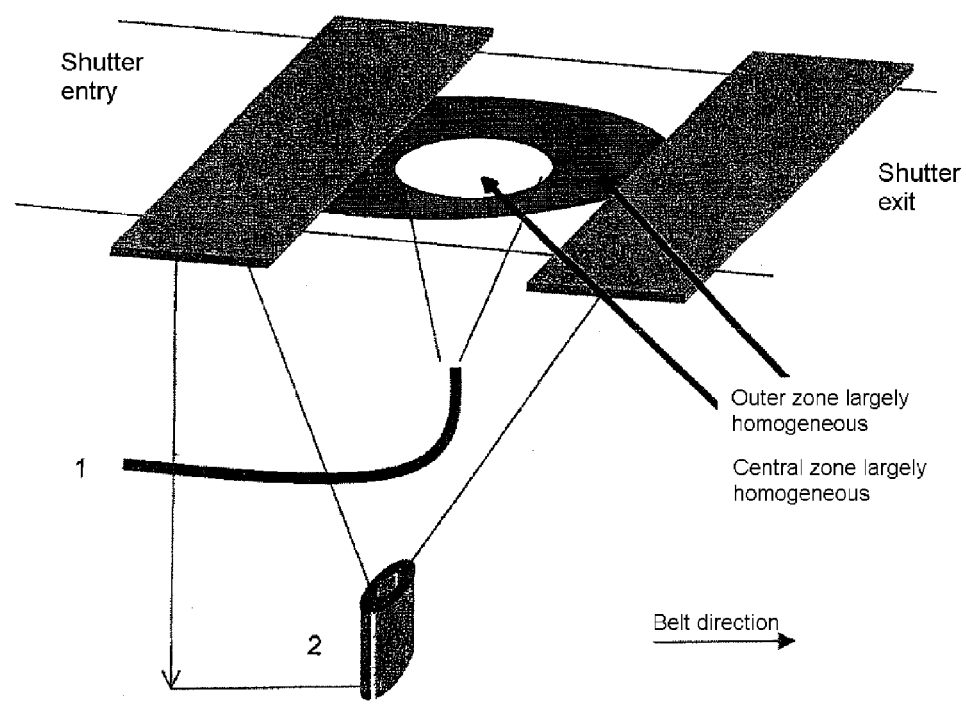
FIG. 15 shows an alternative arrangement to FIG. 9. In contrast to the arrangement as per FIG. 9, the gas inlet is arranged centrally over the vaporization source 2.

An alternative variant is described in FIG. 15. Here, a central, largely oxidic phase is obtained as a result of the central positioning of the oxygen source. Regions of the outer vaporization cone are deposited largely metallically.

A great advantage of these process variants is that a three-layer metallic effect pigment can be prepared in only one single strip pass through the vaporization of metal with different oxygen concentrations in different regions of the vaporization cone.

With the process variants of the invention, therefore, the layer thicknesses and the oxygen content of the individual layers can be efficiently adjusted in a continuous process in one step, in a surprisingly simple way.

It was entirely surprising in this context that the introduction of oxygen, water or oxygen-containing compounds into the regions of the developing vaporization cone that are the outer regions in the case of the vaporization of a metal is sufficient to produce a multilayer film structure in which the outer layers A and C have a larger fraction of oxygen as compared with the middle metallic layer B, and that, following detachment and comminution of this film, metallic effect pigments can be obtained that are of extremely great interest from an optical standpoint.

The three-layer metal film applied to the substrate—a strip-like polymeric film, for example—may be stored and transported in this form. In order to prepare the metallic effect pigments of the invention, the three-layer metal film is detached or removed from a previously applied release layer (separating layer) and at the same time or subsequently is comminuted, in a chemically inert organic solvent, for example. Thereafter the resulting metallic effect pigments of the invention may be concentrated and/or washed in order, for example, to remove residues of the release layer. In another preferred embodiment, the resultant metallic effect pigments of the invention are provided with an anticorrosion layer, made of plastic or metal oxide(s) such as $SiO_2$, for example, and/or with an organic aftercoat, in order to apply functional groups which are able to undergo conversion reaction with binders of a paint system or of an ink, for example.

The metallic pigments of the invention find use in coatings, paints, automobile finishes, powder coatings, printing inks, digital-printing inks, plastics or cosmetic formulations, more particularly in nail varnishes.

The object on which the invention is based is also achieved by means of a coating composition which comprises metallic effect pigments of any of claims 1 to 25.

In accordance with one preferred embodiment, the coating composition is selected from the group consisting of coatings, paints, automobile finishes, powder coatings, printing inks, digital-printing inks, plastics, and cosmetic formulations.

The object on which the invention is based is also achieved by means of a coated article provided with metallic effect pigments of any of claims 1 to 25 or with a coating composition of claim 35 or 36.

The article may be, for example, a vehicle body, a façade element, a printed substrate, such as paper, card, film, etc., or an artificial fingernail.

EXAMPLES

In the text below, the preparation of the effect pigments of the invention is described using examples, without restricting the invention.

Examples 1-4

Figure 3:
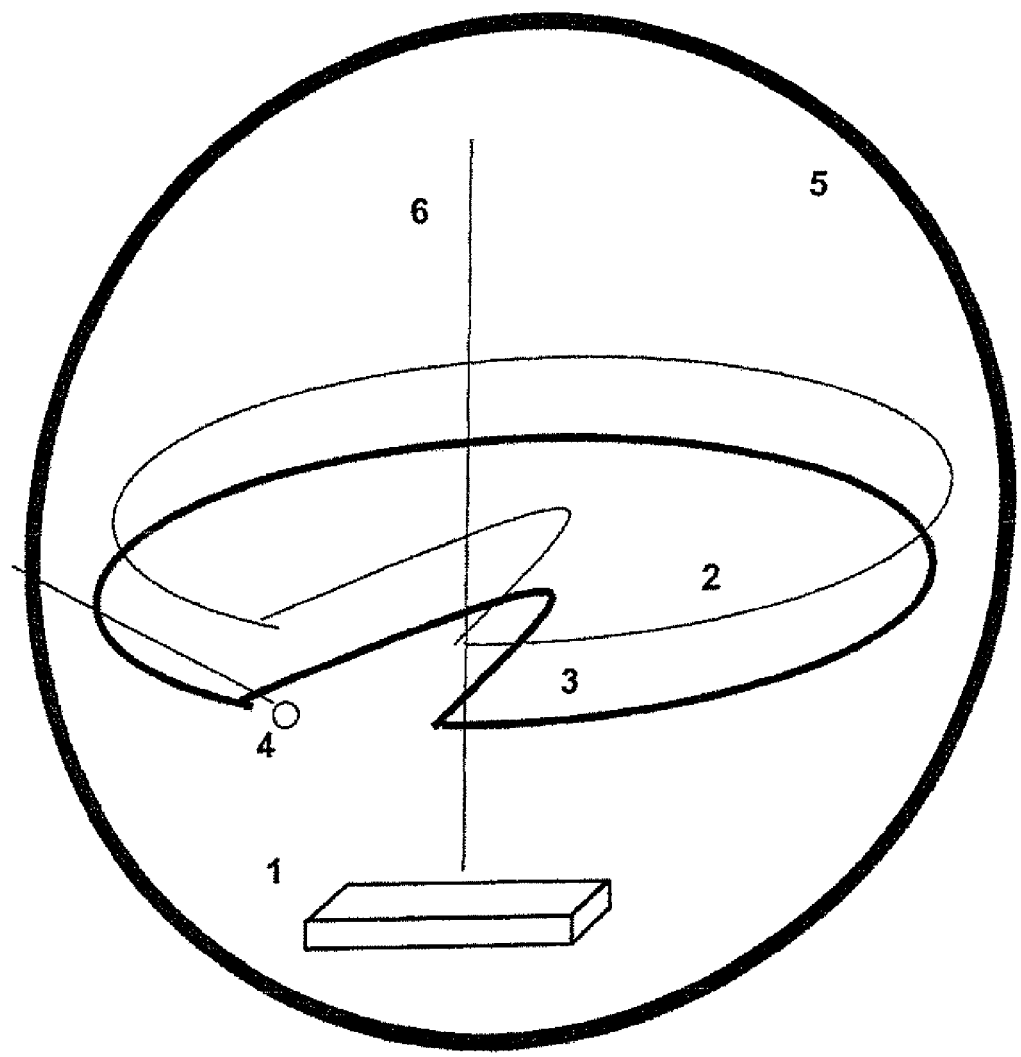
FIG. 3 describes diagrammatically the geometric arrangement in a rotating-plate vaporizer in a vacuum chamber.

The effect pigments of inventive examples 1-4 and of comparative examples 5 and 6 were prepared using a rotary plate unit, as shown in FIG. 3, in three separate coating steps:
General Procedure:
A rotary plate 2 rotatable about an axis of rotation 6 and having a V-shaped cutout is provided with a polyethylene terephthalate (PET) film of 23 μm thickness, which is coated with a release coat, and is arranged in the vacuum chamber 5, as shown in FIG. 3. The release coat is composed of acetone-soluble methyl methacrylate resin and was applied beforehand in a separate workstep. Located between the vaporizer source 1 and the rotary plate 2 provided with the PET film is the fixed shutter 3, which likewise has a V-shaped cutout. The PET film is provided with the release coat on the side facing on the vaporizer source 1. The oscillating quartz 4 protruding into the V-shape cutout in the shutter 4 was used for determining the quantitative metal apply.

Using the PVD laboratory unit shown in FIG. 3, in three passes, in succession, a first layer A of oxide-containing chromium, a second layer B of silver or aluminum, and, finally, a third layer C of oxide-containing Cr were applied. Each of the metals was arranged in the appropriate vaporizer source 1 (see FIG. 3).

The vacuum was generated by two rotary pumps (Edwards) and one diffusion pump (Varian).

The metals used were vaporized by resistance heating. Mass occupancy was controlled on the oscillating quartz (model FTM7, Edwards) via the required heating power for the metal to be vaporized.

The vaporization procedure was monitored so as to produce a constant mass occupancy on the oscillating quartz 4 (see FIG. 3) during coating. Coating duration and chamber vacuum were kept constant during the coating operations.

In the case of the oxidic metallic coatings of layers A and C of the inventive examples, cardboard pieces soaked with water and placed into the vacuum chamber prior to evacuation served as the oxygen source.

The oxygen partial pressure for the respective layers was monitored via the constantly set chamber vacuum, which can be taken from table 1.

Via a data capture program it was possible to record the operational data (mass change on the oscillating quartz, chamber vacuum) in the course of coating.

The vapor deposition rates recorded per second on the oscillating quartz were added up according to coating time in the shutter cutout. Via a conversion factor which takes account of the density of the material applied, it is possible to calculate layer thickness or mass occupancy of the respective layers.

After the end of coating, the vacuum chamber was aerated, the metallized PET film was removed, and the coating was detached from the PET film is a separate detachment unit, using acetone.

By dissolving the release coat layer, the coating was separated from the film. The separated layer stacks were filtered, and the resultant filter cake was washed off fully from the release coat with acetone, converted into a pigment suspension, and comminuted to the desired particle size.

The experimental parameters and the layer thicknesses of the individual layers as calculated by means of the oscillating quartz are reported in table 1.

Inventive Examples 5 and 6

The inventive examples 5 and 6 were prepared by the same process. In contradistinction to inventive examples 1-4, however, aluminum instead of silver was used for layer B. Moreover, no oxygen source was included, resulting in a lower oxide fraction in layers A and C. In these examples, oxygen was incorporated to a lesser extent into the outer Cr layers, a process promoted by the distance of substrate 2 (see FIG. 3) from the vaporization source 1 (45 cm) in the rotary plate unit.

TABLE 1

Experimental parameters for examples 1 to 6 (rotary plate unit) resistance-heated vaporization process

| Sample | Layer sequence/ substances applied | CV [$1 \times 10^{-4}$ mbar] | Mass occupancy [$\mu g \cdot cm^{-2}$] | Layer thickness calculated via the oscillating quartz [nm] |
|---|---|---|---|---|
| Example 1 | A: oxide-containing Cr | 3.44 | 9 | 23 |
|  | B: Ag | 1.32 | 53 | 51 |
|  | C: oxide-containing Cr | 3.84 | 9 | 23 |
| Example 2 | A: oxide-containing Cr | 2.84 | 21 | 41 |
|  | B: Ag | 0.99 | 54 | 51 |
|  | C: oxide-containing Cr | 3.12 | 21 | 41 |
| Example 3 | A: oxide-containing Cr | 3.17 | 13 | 32 |
|  | B: Ag | 1.2 | 53 | 50 |
|  | C: oxide-containing Cr | 2.61 | 13 | 32 |
| Example 4 | A: oxide-containing Cr | 3.63 | 15 | 38 |
|  | B. Ag | 1.2 | 53 | 51 |
|  | C. oxide-containing Cr | 2.39 | 15 | 38 |
| Example 5 | A: Cr | 1.69 | 9 | 24 |
|  | B: Al | 0.82 | 16.6 | 61 |
|  | C: Cr | 0.97 | 9 | 24 |
| Example 6 | A: Cr | 1.21 | 20 | 40 |
|  | B: Al | 0.75 | 13 | 49 |
|  | C: Cr | 0.86 | 20 | 40 |

CV: chamber vacuum

Examples 7 to 9 and 20 to 21

Multistage Strip Process

Examples 7-9 resistance-heated vaporization process
Examples 20-21 vaporization by means of electron beam vaporization The inventive examples 7 and 8 were likewise produced in three coating steps, but with a PVD strip unit, as shown diagrammatically in FIG. 4a. Coating took place in three passes in succession with a first layer A of oxide-containing Cr, with a second layer B of aluminum (example 7) or silver (example 8), and, lastly, with a third layer C of oxide-containing Cr. After coatings A and B, the coated strip was wound back in each case to produce the desired coating sequence.

Comparative example 9 was carried out in the same way. In contrast to inventive examples 7 and 8, aluminum was the metal used for vaporization for each of layers A, B, and C.

Comparative example 20 was carried out in the same way. In contrast to the coatings of inventive examples 7 and 8, the metal vaporized for layers A and C was an iron-chromium alloy produced by means of electron beam vaporizer. The incorporation of oxygen into layers A and C took place with a gas flow regulator (mass flow controller) from MKS in accordance with FIG. 15. For the generation of layer B, aluminum was vaporized by means of electron beam vaporization.

The coating for example 21 took place in the same way as example 20. For the two outer layers, however, titanium was vaporized by means of electron beam vaporization.

The coating substrate used was a 30 cm wide polyethylene terephthalate (PET) film with a thickness of 23 μm, which had been coated with a release coat.

The release coat consisted of acetone-soluble methyl methacrylate resin and was applied in a separate workstep beforehand.

The vacuum, as stated above, was again produced using two preliminary pumps and a diffusion pump. The process parameters are set out in tables 2 and 3 respectively.

The film was moved with the strip speeds reported in tables 2 and 3. Layers A, B, and C of the metals indicated were deposited by vapor deposition onto the moving film. The metals were vaporized using resistance heating for examples 7-9 and by means of electron beam methods (electron beam vaporizer from Telemark, model 272) for examples 20-21. The mass occupancy was monitored by means of an oscillating quartz measurement device, as illustrated in FIG. 4a, model FTM7, Edwards), and the layer thickness was controlled via the heating power and strip speed.

In the case of the oxidic metallic coatings of layers A and C of the inventive examples, cardboard pieces soaked with water and placed into the vacuum chamber prior to evacuation served as the oxygen source.

The oxygen partial pressure for the respective layers was monitored via the constantly set chamber vacuum, (see table 2).

The positioning (in accordance with FIG. 15) of the regulated oxygen feed for the layers of examples 20 and 21 was brought about using a mass flow controller from MKS (see table 3).

For application of the layer B of Al (examples 7, 9, 20, and 21) and of the layer B of Ag (example 8), the procedure was the same. In contradistinction to the coatings A and C, however, there was no supply of oxygen.

The precise parameters and the layer thicknesses calculated by means of the oscillating quartz, and/or the mass occupancies resulting therefrom of the individual layers A, B, and C of the inventive pigments, can be found in table 2 and table 3.

Figure 5:
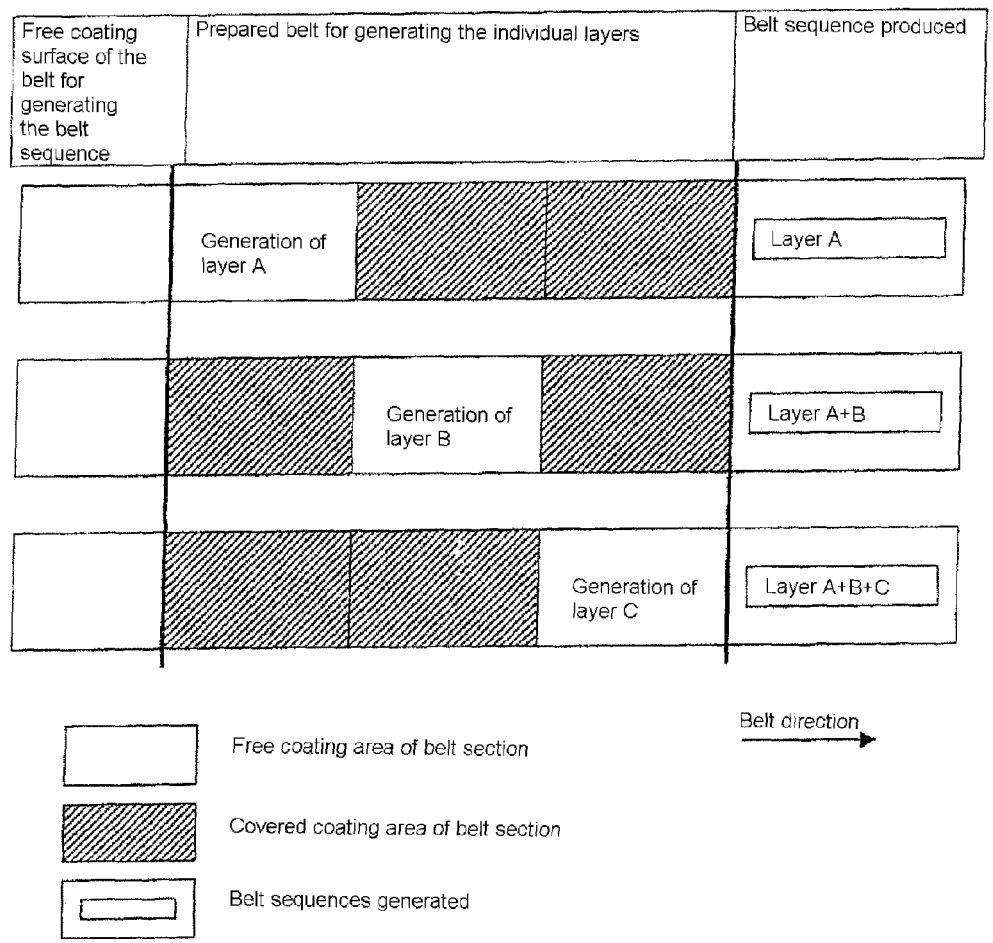
FIG. 5 shows how in principle the three layers A, B, and C can be prepared by stepwise vapor deposition. The belt is wound back in each case after coating of A and coating of B, in order to be able to produce not only the individual layers but also the complete layer sequence A-B-C. This procedure is advisable especially when using different metals for A or B or C.

In order to allow better determination, in addition, of the oxygen content of the individual layers A, B, and C and of the complete layer sequence A-B-C, the film to be coated, as shown diagrammatically in FIG. 5, was prepared in examples 7, 20, and 21 by means of suitably placed shutters during the coating operations. By this means, certain film sections were coated exclusively with only one layer A, B or C in each case, and were analyzed separately later on. In the section without shutters, all three layers were deposited.

At the end of coating, the vacuum chamber was aerated, the metallized PET film was removed, and the coating was removed from the PET film in a separate detachment unit, using acetone.

In this operation the coating was removed from the film by dissolution of the release coat layer. The separated layer stacks were filtered and the resultant filter cake was washed completely from the release coat using acetone, converted into a pigment suspension, and comminuted to the desired particle size.

Examples 10, 11, and 13

Single-Stage Strip Process

Examples 10, 11, and 13 resistance-heated vaporization process

Examples 22, 23, and 24 vaporization by means of electron beam vaporization

To produce the colored metallic effect pigments of the invention of inventive examples 10, 11, 13, and 22, 23, and 24, an inventive PVD strip process was used in which a three-layer metallic pigment was produced in only one pass. In this case the entire vacuum chamber was equipped in each case with the following oxygen sources: for example 10, a constant oxygen partial pressure was generated by a constant feed of air into the vacuum chamber. In the case of example 11, wet cardboard was positioned to the left and right of the shutter entrance and the shutter exit (see FIG. 9).

For the positioning in the case of example 13, two pieces of soaked card as an oxygen source were brought up close to the vaporization cone. The radiant heat from the vaporizer produced a high sublimation stream of water from the two water-soaked cardboard pieces into the metal cone.

The positioning (in accordance with FIG. 15) of the regulated oxygen feed for examples 22, 23, and 24 was brought about using a mass flow controller from MKS.

FIG. 4a shows the coating apparatus diagrammatically. Critical here is the fact that, as a function of the distance of the vaporizer source from the coating strip, two relatively sharply distinguishable regions can be imagined on the coating strip, with layers differing in oxygen content (see FIG. 9 and FIG. 15).

Figure 16:
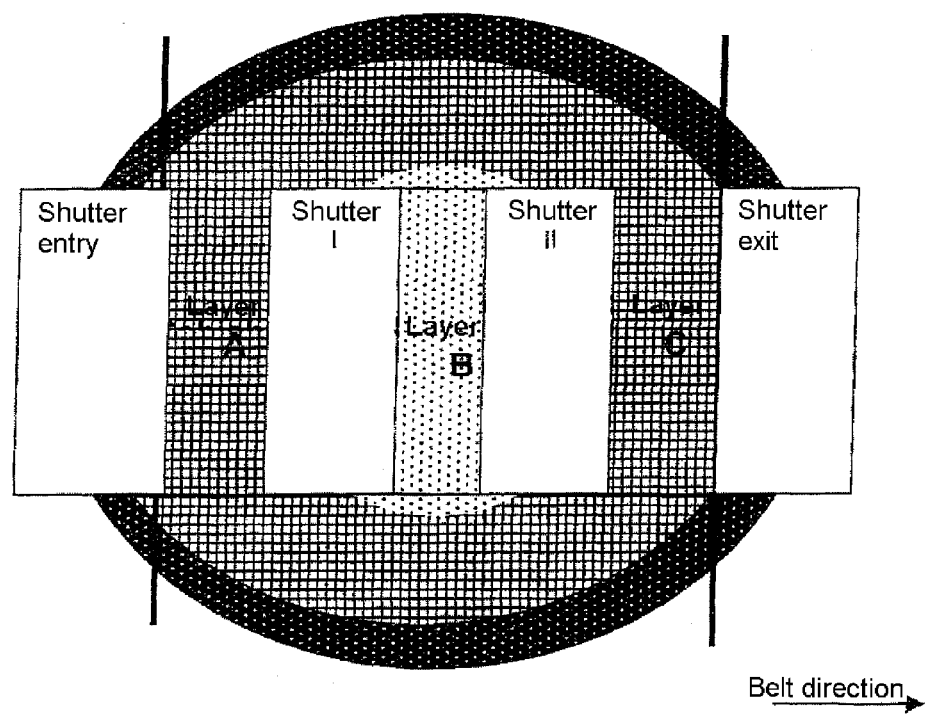
FIG. 16 shows an inverse arrangement of the vapor-deposited layers relative to the arrangement of the layers as per FIG. 10, with the oxygen content being lower in layers A and C than in layer B. In this case, layers A and C are largely metallic, and layer B is largely oxidic.

FIG. 10 and FIG. 16 each show, in a diagrammatically plan view (from the viewpoint of the vaporizer source), a shutter arrangement between vaporizer source and coating strip. Through the selection of suitable shutters (width, length) and the precise positioning of the shutters, it was possible to subdivide the coating strip into three separate coating zones, in each of which only layers A, B, and C were formed.

In order to allow a precise determination of the layer thicknesses and of the oxygen contents of the individual layers, A, B, and C in their respective zones, and also of the complete layer sequence A-B-C, very narrow shutters running parallel to the strip direction (longitudinal shutters) were incorporated additionally in the case of examples 10, 22, 23, and 24 (see FIG. 11 and FIG. 17), and by means of this measure, after the travel of the strip substrate, regions with the layers A, B, and C, in each case separately, and also the complete layer structure A-B-C, were applied to the strip substrate. The geometric arrangement of the transverse shutters and longitudinal shutters in accordance with FIGS. 11 and 17 can be seen in table 4.

In the case of examples 11 and 13, in contradistinction to examples 10, 22, 23, and 24 (see plan view diagrammatic FIG. 10), there was no separation by shutters into three coating regions.

Coatings were carried out using a 30 cm wide polyethylene terephthalate (PET) film with a thickness of 23 µm which is coated with a release coat.

The release coat consisted of acetone-soluble methyl methacrylate resin and was applied in a separate workstep beforehand.

The vacuum was generated in each case by means of two preliminary pumps and a diffusion pump, as described above.

For examples 10, 11, and 13, a single vaporizer source of resistance-heated aluminum was used. The layer thickness of the central Al layer A was controlled via the amount of Al wire conveyed into the vacuum chamber from the outside, via the size of the central shutter cutout, via the heating power of the vaporizer ceramic used, and by the strip speed.

For examples 22, 23, and 24, Cr (example 22), Ag (example 23), and Cu (example 24) were vaporized in accordance with the process parameters of table 3 by means of an electron beam vaporizer from Telemark, model 272.

The layer thickness of the central layers B was controlled via the respective emission streams at constant acceleration voltage, via the sizes of the central shutter cutouts for each of examples 22, 23, and 24, and via the respective strip speeds.

The layer thickness for examples 10, 11, and 13 and 22, 23, and 24 and the oxide content of the layers A and C was monitored by means of the shutter arrangement and also the amount of oxygen supplied. The experimental parameters are given in table 2 and table 3.

After coating was at an end, the vacuum chamber was aerated and the metallized PET film was withdrawn.

The coated films of examples 10, 22, 23, and 24 each showed four longitudinal strips of layers A, B, and C, which stood out significantly in color from the complete layer sequence A-B-C. The film sections of coatings A, B, and C and also the complete layer sequence A-B-C were cut from one another and detached from the PET film with acetone in separate detachment units in each case.

The pigments of examples 11 and 13 were prepared in accordance with the diagrammatic representation of the process in FIG. 9 and with the above-described procedure in accordance with the process parameters in table 2, but without the two narrow extra shutters I and II and without the longitudinal shutters.

Analytical Oxygen Determination
EDX Measurements:

The composition of oxygen and metal of the pigments of examples 7, 10, and 20-24 were determined using the above-described measurement methodology by means of EDX (instrument: EDAX Gemini; EDAX Incorp., USA) on the individual layers.

Sample Preparation:

A few drops of the pigment suspension were applied to the sample plate, and the solvent was slowly evaporated at room temperature. The pigments take up an orientation largely parallel to the plate surface.

Using the pigments of example 10, a depth profile of the inventive effect pigment was produced (see FIG. 6). Moreover, the atomic ratio of oxygen to metal was determined on individual layers of the inventive effect pigment from example 10 (see table 5).

The excitation energy of the electron beam determined the depth of penetration into the pigment (cf. FIG. 2). For oxygen, the $K_\alpha$ line (excitation energy: about 0.5 keV), for chromium the $L_\alpha$ line (excitation energy: about 0.6 keV), and for aluminum the $K_\alpha$ line (excitation energy: about 1.5 keV) were excited.

The detailed procedure was as follows:

By carrying out stepwise increase of the irradiated electron energy, the depth of penetration of the electron beam into the sample was continually increased. At the same time, the EDX analysis was used to investigate which elements were excited. In this way it was possible to find exactly the layer thickness (or depth of penetration) from which the elements of the second and third layers are detectable. For the purpose of analysis, the spectra then employed were only those which represent the signals of the first layer, of the second layer, and, finally, of the third layer. In the case of the third layer, however, signals of the first layer, originating from underlying pigments, were obtained again. The signals for this layer were therefore no longer able to be fully resolved.

In the case of the chromium-containing samples, the partially overlapping peaks (Cr and O peaks) were evaluated by means of the instrument's own software program (version 3.60) by means of a holographic peak deconvolution analysis (HDP).

ESCA/XPS Measurements:

Additionally, the pigments of example 8 and of example 9 were studied by means of ESCA for their elemental composition and for their metal content and oxygen content. For sample preparation, the pigments were taken up in acetone and dried down on a glass support. In this way, a largely plane-parallel orientation of the pigments is achieved. The measurements were carried out using the Thermo VG Scientific ESCALAB 250 instrument. Excitation took place using monochromatic Al $K_\alpha$ x-ray radiation (15 kV, 150 W, 500 µm spot size). The transmission function of the instrument was measured on a copper sample. Charge compensation took place using a "flood gun" with an electron energy of 6 eV/0.05 mA beam current.

First of all an overview spectrum (pass energy: 80 eV) was recorded. Subsequently, high-resolution spectra were measured, with a pass energy of 30 eV. The samples were sputtered off with Ar ions, and then a high-resolution spectrum was measured using the ESCALAB 250. In this way, depth profiles of the composition were defined.

The average layer thicknesses of the samples were determined by counting a significant random sample (>20 particles) under a scanning electron microscope (SEM). In this case, the azimuthal angles of the individual pigment particles relative to the plane of the viewer were estimated and included in the calculation. Only particles standing largely perpendicular to the plane of the viewer were subjected to measurement.

Figure 8:
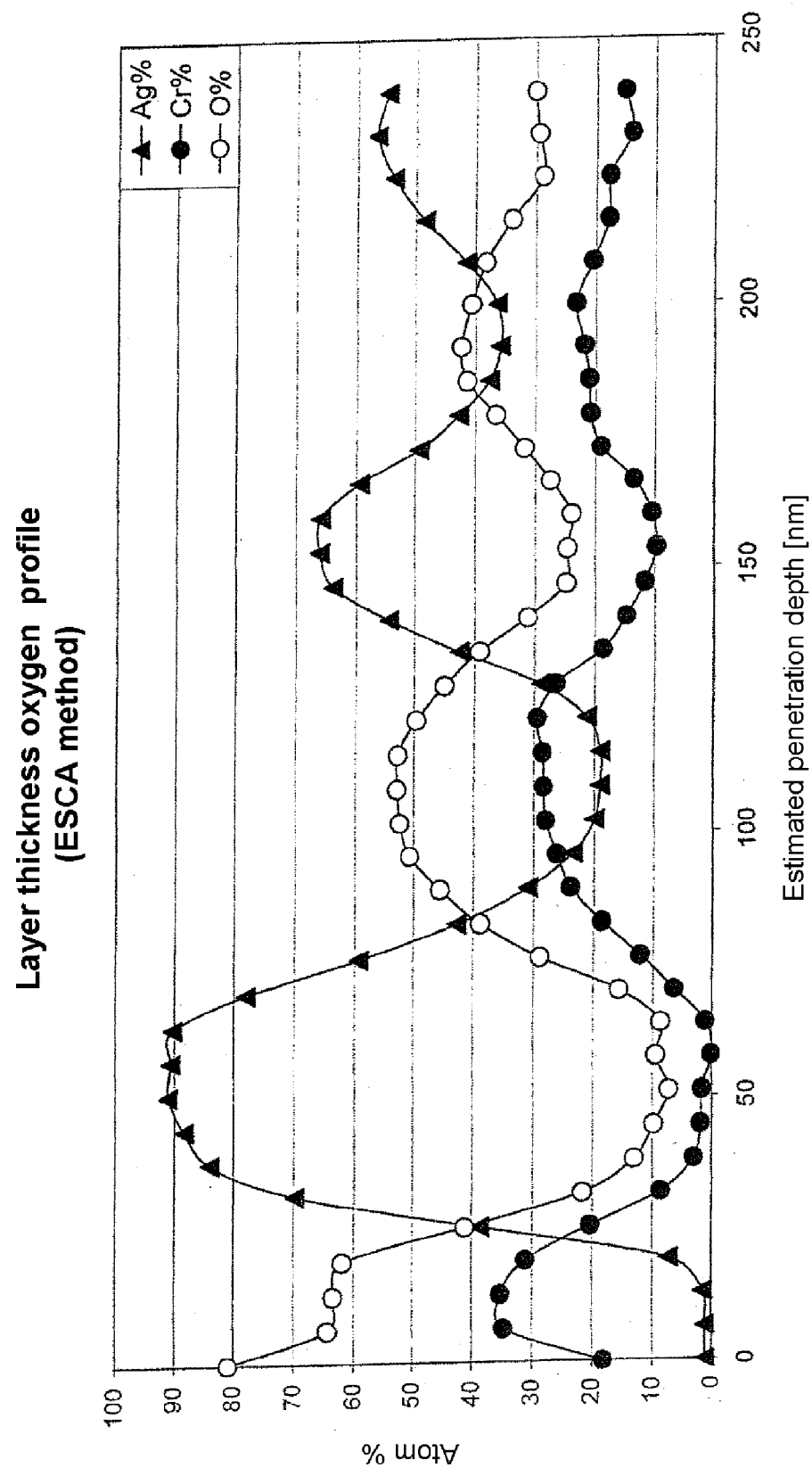
FIG. 8 represents by way of example the layer thickness profile and oxygen profile, determined by the ESCA method, for the case where the metal used is the same for layers A and C, but different from B.

FIG. 8 shows the concentrations of the elements silver, chromium, and oxygen as a function of the sputter depth. The sputter depth is given only approximately and can only be roughly estimated, since an absolutely precise calibration was not possible. Consequently, this depth scale does not necessarily match the layer thicknesses determined from SEM measurements. Distinctly in evidence first of all is a Cr—O layer. At a sputter depth of about 50 nm, the chromium signal has dropped virtually to the zero point, and, correspondingly, the silver signal has risen from almost zero to more than 90 atom % (layer B). Subsequently (at about 100 nm sputter depth), the silver signal drops off again, and the chromium signal and oxygen signal increase again, but without reaching the same values as at the start; in particular, the drop in the silver signal is not as great.

It is thought that fluctuations in the measurement method, in sputtering and/or the statistical distributions of the layer thicknesses of the pigments cause "smudging" of the signals. The initial values, however, represent reliable figures for the average composition of the layers A and B.

The reason for the subsequent increase in the silver signal, followed by an increase in the chromium signal, is that the next layer of pigments has already been measured and the first layer of pigment has already been largely sputtered away. Overall, as the number increases, the element concentrations measured naturally level to an increasing extent.

The layer structure of the pigments can be analyzed, furthermore, in a specific way by means of SEM transverse ground sections.

FIG. 7 shows the layer structure of the pigment of inventive example 9 as determined by means of ESCA/XPS measurements. In the outer layers there is on average an aluminum concentration of 53 atom % and a corresponding oxygen concentration of 47 atom %. After a sputter depth of about 50 nm, the aluminum signal begins to grow and the oxygen signal, correspondingly, to fall. At its maximum, the Al concentration reaches 71 atom %.

Example 12

Process with Three Vaporization Sources

The experimental apparatus used was the same as for inventive examples 10 and 11. To produce the layer B, aluminum was subjected to resistance-heated vaporization with continuous wire feed. Additionally, however, closely adjacent to the vaporizer ceramic, two molybdenum boats were attached for the vaporization of Cr (FIG. 4b). As an oxygen source, wetted cardboard pieces were inserted into the vacuum chamber.

The layer thickness of the central Al layer A was controlled via the amount of Al wire fed to the vacuum chamber from outside, via the size of the central shutter cutout, via the heating power of the vaporizer ceramic used, and via the strip speed.

The layer thickness and the oxide content of the layers A and C of Cr were regulated by the shutter arrangement and by the variably adjustable resistance of the molybdenum boats, and also the amount of oxygen supplied. When coating was at an end, the vacuum chamber was aerated and the metallized PET film was removed and subjected to further processing as described in the other examples.

Metal pigments are obtained which have a pale gold luster and an extremely strong light-dark flop.

Comparative Example 14

Imperial Gold 629261G, commercially available brass pigment (manufacturer: ECKART GmbH).

Comparative Example 15

Variocrom Magic Gold (BASF)
Commercially available five-layer interference effect pigment with a core of aluminum, an $SiO_2$ layer on both sides, and a semitransparent iron oxide layer. The average particle size is 17 μm.

Comparative Example 16

Commercially available Gold Leaf.
Best Rosenobel Double Gold 23% carats; Noris Blattgold).

Comparative Example 17

Gold was sputtered in a layer thickness of about 80 nm onto a slide.

Finally, after uniform comminuting methods, customary laser diffraction techniques (instrument: Cilas 1064) were used to determine the size distribution of the pigments of examples 1-8, 10-13, 23, 24, and the comparative examples and to determine, in customary manner, from the cumulative undersize distribution, the $D_{50}$ value as a measure of the average size (see table 5).

TABLE 2

Process parameters and calculated layer thicknesses for examples 7 to 13 (stripcoating unit; resistance-heated vaporization process)

| Sample | Layer sequence/ substances applied | Chamber vacuum $[1*10^{-4} \text{ mbar}]$ | Mass occupancy $[\mu g*cm^{-2}]$ | Layer thickness calculated via the oscillating quartz [nm] | Strip speed $[m*min^{-1}]$ |
|---|---|---|---|---|---|
| Example 7 | A: Oxide-containing Cr | 6.5 | 10.5 | 28 | 0.8 |
|  | B: Al | 0.9 | 11.0 | 41 | 0.8 |
|  | C: Oxide-containing Cr | 5.0 | 10.5 | 28 | 0.8 |
| Example 8 | A: Oxide-containing Cr | 4.0 | 9.8 | 25 | 0.64 |
|  | B: Ag | 1.0 | 113 | 110 | 3 |
|  | C: Oxide-containing Cr | 3.5 | 9.8 | 25 | 0.64 |
| Example 9 | A: Oxide-containing Al | 2.0 | 19.6 | 73 | 0.64 |
|  | B: Al | 1.43 | 17.3 | 64 | 0.64 |
|  | C: Oxide-containing Al | 1.8 | 23 | 86 | 0.64 |
| Example 10 | A: Oxide-containing Al |  |  |  |  |
|  | B: Al | 3.0 |  |  | 1.2 |
|  | C: Oxide-containing Al |  |  |  |  |
| Example 11 | A: Oxide-containing Al |  |  |  |  |
|  | B: Al | 25 |  |  | 20 |
|  | C: Oxide-containing Al |  |  |  |  |
| Example 12 | A: Oxide-containing Cr |  |  |  |  |
|  | B: Al | 13 |  |  | 8.0 |
|  | C: Oxide-containing Cr |  |  |  |  |
| Example 13 | A: Oxide-containing Al |  |  |  |  |
|  | B: Al | 500 | 68 |  | 20 |
|  | C: Oxide-containing Al |  |  |  |  |

TABLE 3

Process parameters for examples 20 to 24 (stripcoating unit - vaporization process with electron beam vaporization)

| Sample | Layer sequence/ substances applied | Chamber vacuum $[1*10^{-4} \text{ mbar}]$ | Mass occupancy $[\mu g*cm^{-2}]$ | Gas flow $[sl*min^{-1}]$ | Emission current [mA] at 10 kV | Strip speed $[m*min^{-1}]$ |
|---|---|---|---|---|---|---|
| Example 20 | A: Oxide-containing Fe/Cr | 5.5 | 15.3 | 1.1 | 460 | 22 |
|  | B: Al | 1.2 | 10.8 | 0 | 400 | 22 |
|  | C: Oxide-containing Fe/Cr | 3.7 | 15.3 | 1.1 | 480 | 22 |

TABLE 3-continued

Process parameters for examples 20 to 24 (stripcoating unit - vaporization process with electron beam vaporization)

| Sample | Layer sequence/ substances applied | Chamber vacuum [1*10⁻⁴ mbar] | Mass occupancy [μg*cm⁻²] | Gas flow [sl*min⁻¹] | Emission current [mA] at 10 kV | Strip speed [m*min⁻¹] |
|---|---|---|---|---|---|---|
| Example 21 | A: Oxide-containing Ti | 2 | 15.4 | 0.1 | 440 | 3.2 |
| | B: Al | 0.9 | 16.2 | 0 | 275 | 3.2 |
| | C: Oxide-containing Ti | 1.5 | 15.4 | 0.1 | 520 | 3.2 |
| Example 22 | A: Oxide-containing Cr | 1.7 | 55.5 | 0.65 | 450 | 6.5 |
| | B: Oxide-containing Cr | | | | | |
| | C: Oxide-containing Cr | | | | | |
| Example 23 | A: Oxide-containing Ag | 2.2 | 16.3 | 0.3 | 340 | 6.5 |
| | B: Oxide-containing Ag | | | | | |
| | C: Oxide-containing Ag | | | | | |
| Example 24 | A: Oxide-containing Cu | 10 | 21.9 | 0.7 | 350 | 4 |
| | B: Oxide-containing Cu | | | | | |
| | C: Oxide-containing Cu | | | | | |

Figure 11:
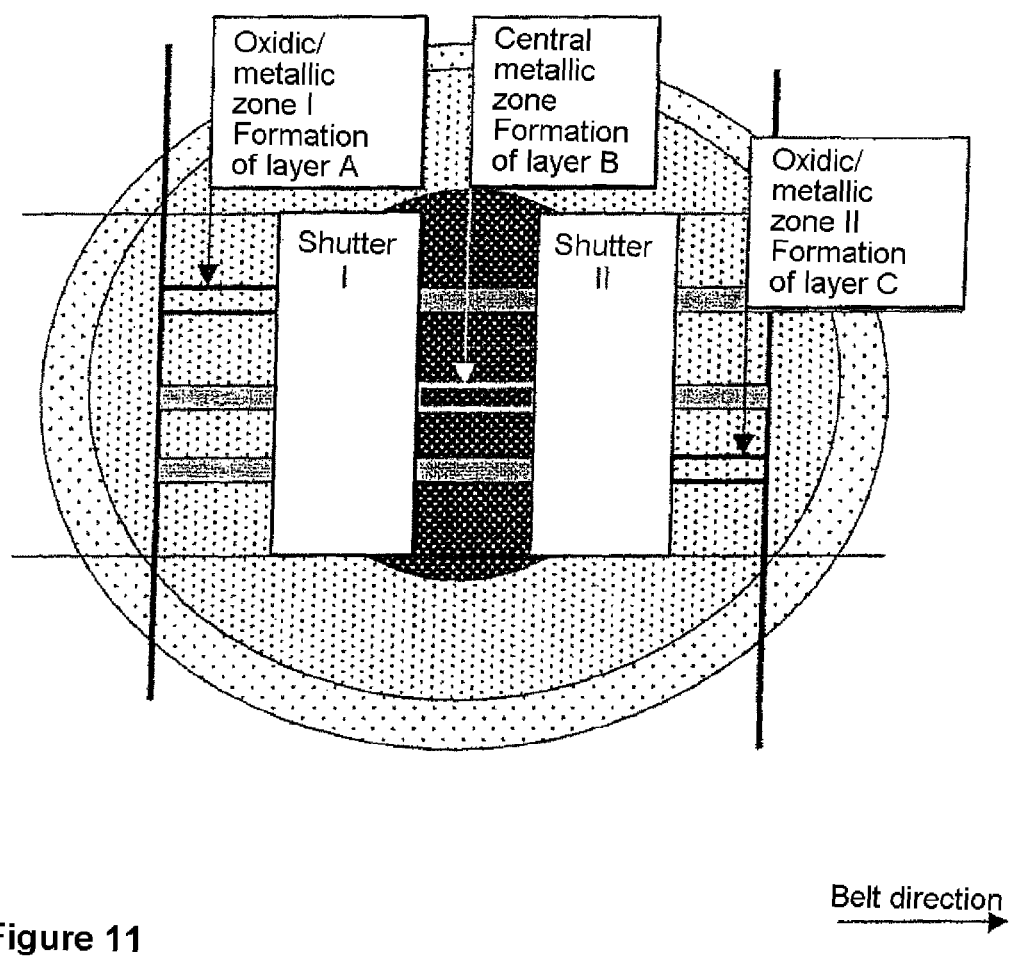
FIG. 11 shows the preparative shielding of a striplike substrate by horizontal and vertical shutters I and II, which ultimately produce the coating of the individual layers A, B, and C, and also of the overall layer sequence A-B-C simultaneously on metallization. Layers A and C are largely oxidic, and layer B is largely metallic.
Figure 17:
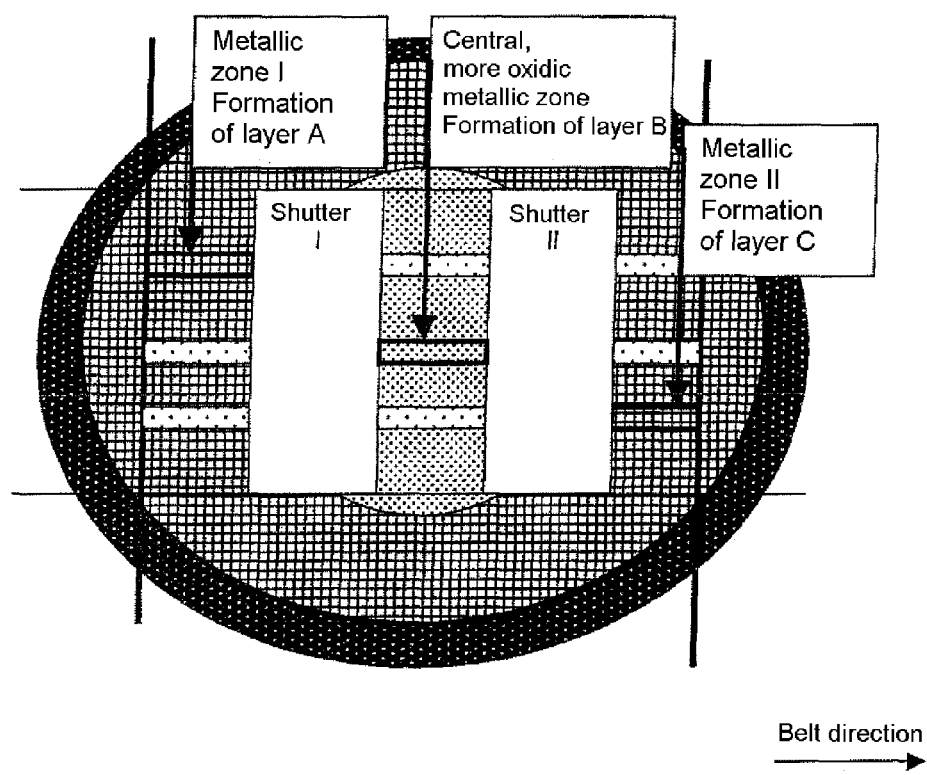
FIG. 17 shows an inverse arrangement of the vapor-deposited layers relative to the arrangement of the layers as per FIG. 11, with the oxygen content being lower in layers A and C than in layer B. In this case, layers A and C are largely metallic, and layer B is largely oxidic.

TABLE 4 geometric dimensions of the plan view of FIGS. 11 and 17 at a distance of vaporization source from substrate of 40 cm.

| | Longitudinal shutter for zone I | Transverse shutter I | Longitudinal shutter for central zone | Transverse shutter II | Longitudinal shutter for zone II |
|---|---|---|---|---|---|
| Example 10 | Open 19 cm | Closed 15 cm | Closed 8 cm | Closed 10 cm | Closed 10 cm |
| | Closed 19 cm | Closed 15 cm | Open 8 cm | Closed 10 cm | Closed 10 cm |
| | Closed 19 cm | Closed 15 cm | Closed 8 cm | Closed 10 cm | Open 10 cm |
| Complete layer sequence example 10 | Open 19 cm | Closed 15 cm | Open 8 cm | Closed 10 cm | Open 10 cm |
| Example 22 | Open 5 cm | Closed 7.5 cm | Closed 15 cm | Closed 7.5 cm | Closed 5 cm |
| | Closed 5 cm | Closed 7.5 cm | Open 15 cm | Closed 7.5 cm | Closed 5 cm |
| | Closed 5 cm | Closed 7.5 cm | Closed 15 cm | Closed 7.5 cm | Open 5 cm |
| Complete layer sequence example 22 | Open 5 cm | Closed 7.5 cm | Open 15 cm | Closed 7.5 cm | Open 5 cm |
| Example 23 | Open 9 cm | Closed 7.5 cm | Closed 7.5 cm | Closed 7.5 cm | Closed 9 cm |
| | Closed 9 cm | Closed 7.5 cm | Open 7.5 cm | Closed 7.5 cm | Closed 9 cm |
| | Closed 9 cm | Closed 7.5 cm | Closed 7.5 cm | Closed 7.5 cm | Open 9 cm |
| Complete layer sequence example 23 | Open 9 cm | Closed 7.5 cm | Open 7.5 cm | Closed 7.5 cm | Open 9 cm |
| Example 24 | Open 9 cm | Closed 7.5 cm | Closed 7.5 cm | Closed 7.5 cm | Closed 9 cm |
| | Closed 9 cm | Closed 7.5 cm | Open 7.5 cm | Closed 7.5 cm | Closed 9 cm |
| | Closed 9 cm | Closed 7.5 cm | Closed 7.5 cm | Closed 7.5 cm | Open 9 cm |
| Complete layer sequence example 24 | Open 9 cm | Closed 7.5 cm | Open 7.5 cm | Closed 7.5 cm | Open 9 cm |

Colorimetric Properties from Applicator Drawdowns

The colorimetric characteristics of the pigments of the inventive examples and of the comparative examples are shown below.

For this purpose, each pigment was stirred into 2 g of a conventional nitrocellulose varnish (Dr. Renger Erco Bronzemischlack 2615e, Morton). The effect pigment was introduced first and then dispersed into the varnish using a brush.

The completed varnish was applied on an applicator drawdown device at a wet film thickness of 50 μm to No. 2853 test charts from Byk Gardner (black/white contrast paper).

The level of pigmentation was selected so as to produce a hiding coat. As a result, the effect of the background is excluded from the colorimetric data.

The applicator drawdowns were measured colorimetrically in accordance with manufacturer specifications (Optronic Multiflash instrument, Berlin). Irradiation took place at a constant angle of 45°, and the CIELAB L*, a*, and b* values were determined at viewing angles of 15°, 20°, 25°, 45°, 55°, 70°, 75°, and 110° relative to the specular angle (illuminant: D65).

Entered in table 5 in addition to analytical data are the colorimetric data for the applicator drawdowns of the inventive examples and the comparative examples.

Figure 12:
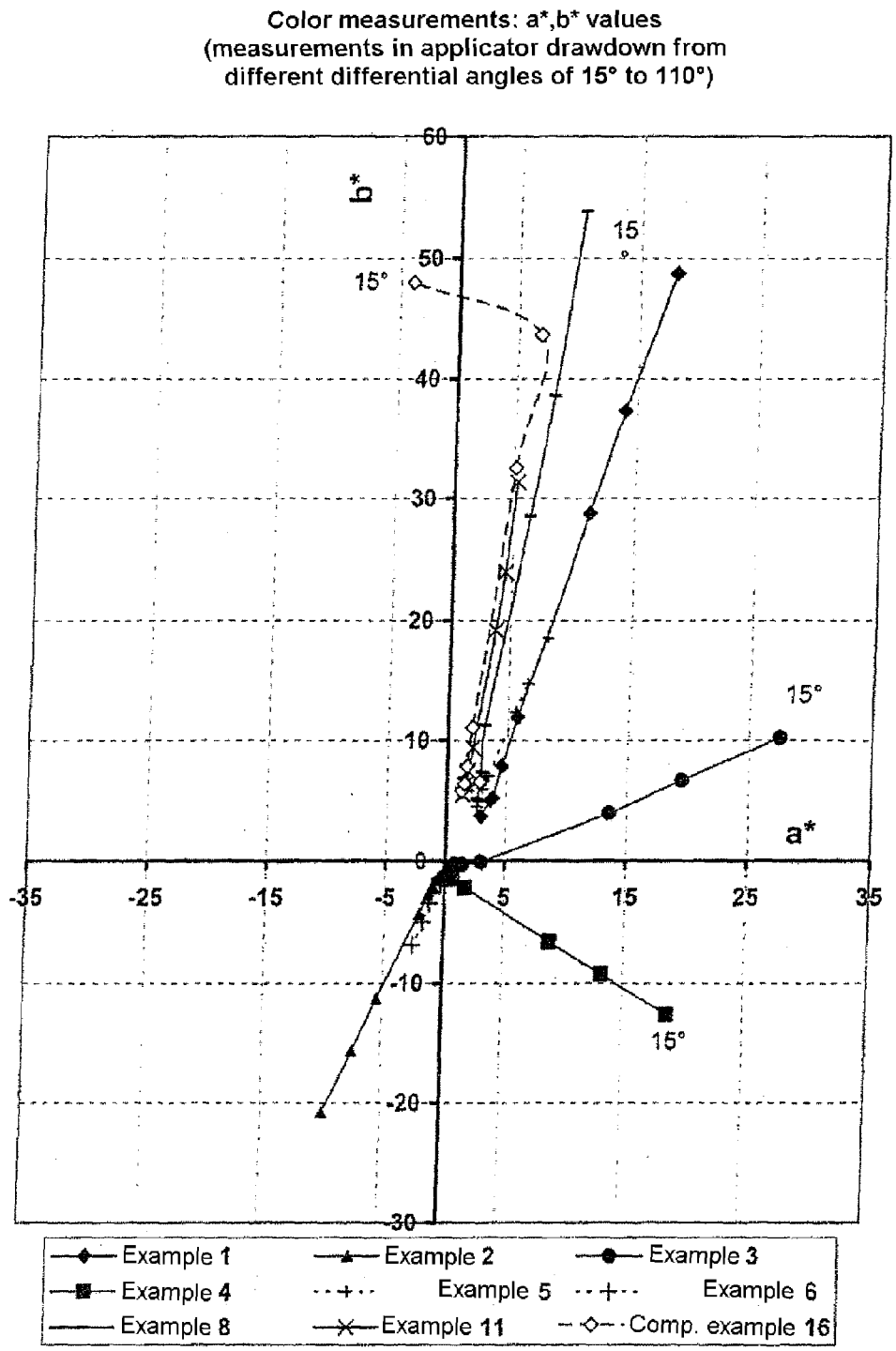
FIG. 12 shows by way of example the colorimetric representation of metallic golden, blue, violet, and red effect pigments of the invention in the a*, b* color space, and the color saturation effect of the oxide-containing layers A and C in comparison to layers A and C with a lower oxide fraction.

FIG. 12, in a CIELAB a*, b* representation, shows the colorimetric representation of inventive pigments and pigments from comparative examples. Additionally a gold leaf specimen (comparative example 16, Bestes Rosenobel Double Gold 23% carats; Noris Blattgold) was subjected to measurement.

The pigments of examples 1, 8, and 11 show metallically gold-colored effects. Correspondingly, example 2 appears blue, example 3 red, and example 4 violet, with color flop effects.

The samples of inventive examples 5 and 6 show a more discreet chroma than those of inventive examples 1 and 2.

Comparative example 16 (gold leaf) likewise shows a strong chroma, but has a slight color flop (measurement angle 15° to 20°) and hence a lower purity of hue than the pigments of the invention.

The pigment according to example 11, produced by coating in one vapor-coating step, exhibits in its profile a conformity to the profile of the gold leaf specimen in the yellow region (comparative example 16), but does not attain the chroma of the gold leaf. Example 8 likewise shows a conformance of the curve profile to the gold leaf specimen, and, furthermore, exhibits a significantly stronger chroma than the gold leaf specimen.

The pigments of examples 5 and 6 have a more discreet chroma.

Figure 13:
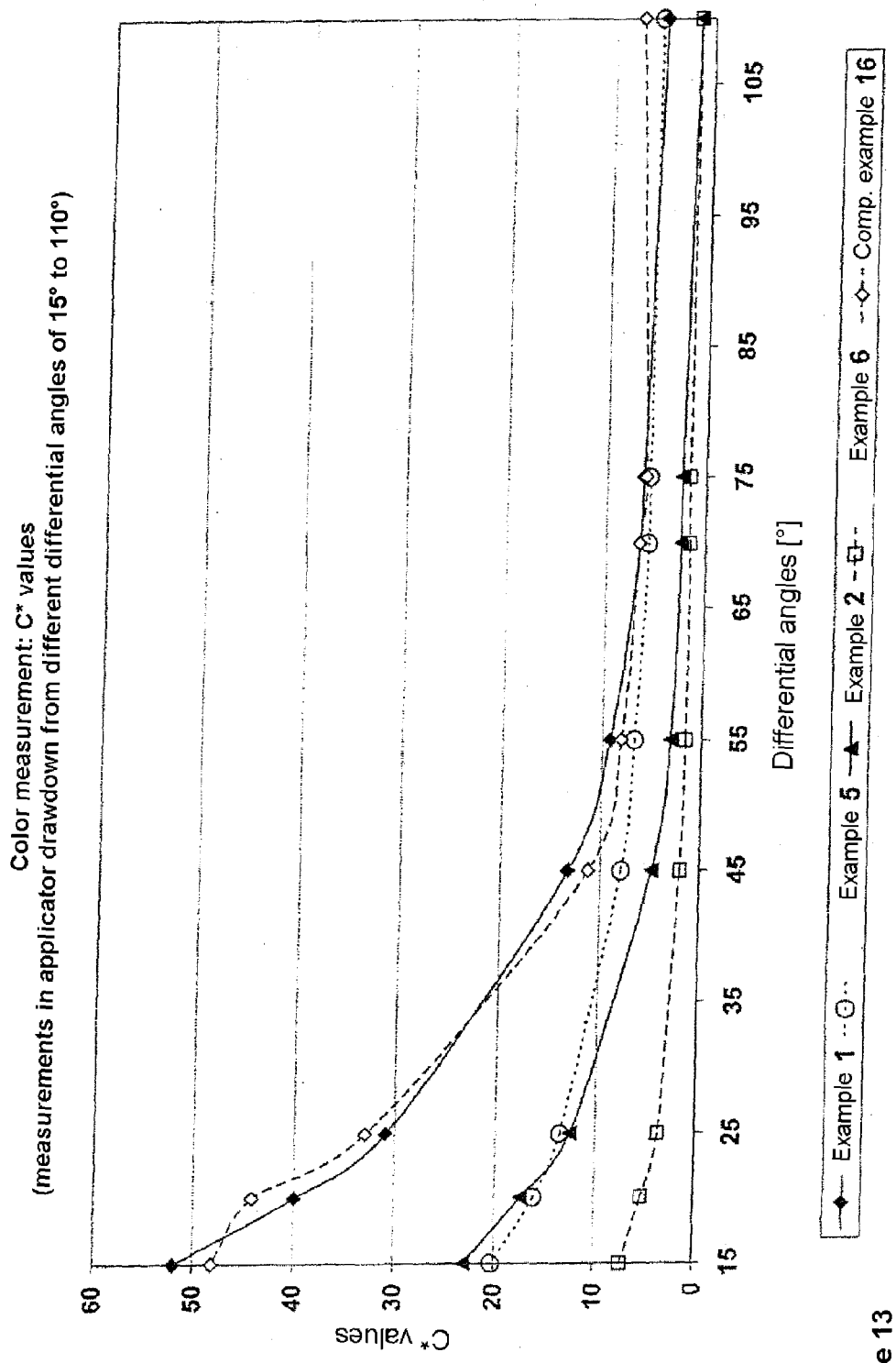
FIG. 13 shows by way of example the intensification of the chroma in the case of golden and blue metallic effect pigments as a result of the higher oxide fraction in layers A and C.

Depicted in FIG. 13 is the chroma of different gold-colored (example 1, example 5) and blue (example 2 and example 6) metallic effect pigments with respect to the specular angle. This representation shows that the strong color chroma of gold leaf is also achieved by the inventive pigment of example 1. Examples 5 and 6 (Cr/Al/Cr) have a more discreet chroma even close to the specular angle (15°), of not more than 20 units.

Figure 14:
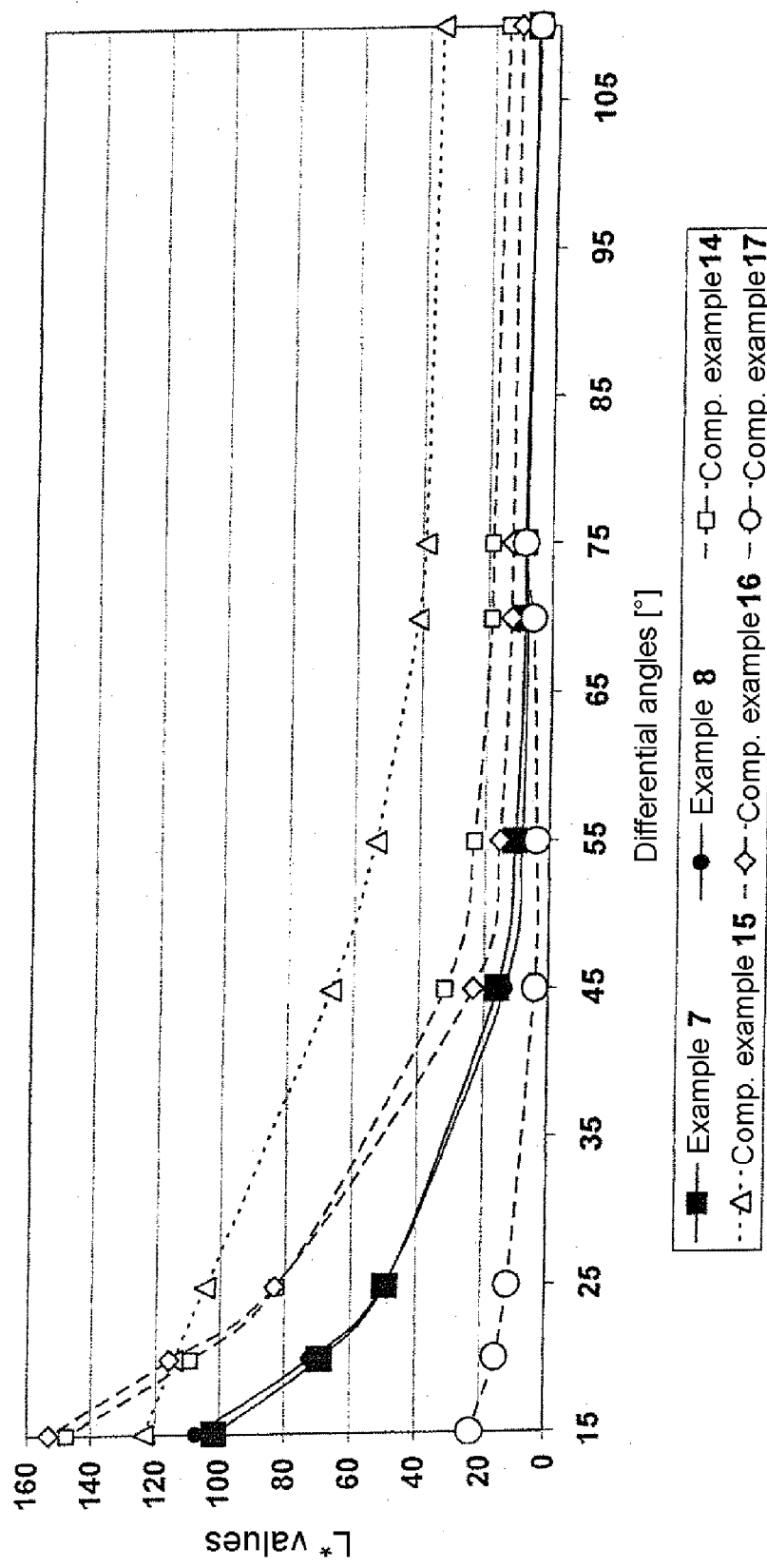
FIG. 14 shows the lightness values plotted as a graph over different angles. This representation is intended to underline the mirrorlike nature of the effect pigments of the invention.

FIG. 14 shows in the form of a graph the lightness values across various viewing angles of different gold-colored inventive and comparative examples. In this case, inventive examples 7 and 8, and also prior-art samples such as brass pigments (comparative example 14), Variochrom (comparative example 15), and the gold leaf specimen (comparative example 16) were used. Moreover, a slide was coated with gold in a sputtering process and hence given a mirror coating (comparative example 17), which was measured.

The lightness curves of example 7 and 8 exhibit an extremely sharp drop to low values at higher viewing angles. This effect is attributable primarily to the high oxygen content of the outer layers A and C of these pigments. These layers have a dark coloration. The pigments of comparative examples 14 to 16 show higher L* values at 15°, but at higher angles do not attain the low values of the inventive examples. The gold sputtered onto the slide (comparative example 17) appears as a gold mirror and, accordingly, has an extremely high gloss. The lightness at 15° measured on this sample is very low, since in this case virtually all of the incident light was reflected at the specular angle and there is hardly any radiation scattering. Appearing all the more remarkable, therefore, are the lightnesses of the inventive examples at high measurement angles, said lightnesses being comparably low to the gold mirror.

The extremely sharp change in lightness from light to dark in the pigments according to the invention is also reflected in the very high flop indices (table 5).

TABLE 5

| Sample | | Layer sequence of vapor-deposited metal | | | Measurement methodology | | Level of pigmentation [%] | D 50: [μm] | Lightnesses | | | Flop | Subjective perceived color |
|---|---|---|---|---|---|---|---|---|---|---|---|---|---|
| | | | | | EDX | ESCA | | | L15 | L45 | L110 | | |
| Example 1 | | Cr | Ag | Cr | | | 8.8 | 15 | 86.8 | 14.2 | 5.9 | 36 | 50 μm drawdown with very intense-colored gold-brown luster |
| | Layer thicknesses [nm] | 23 | 50 | 23 | | | | | | | | | |
| Example 2 | | Cr | Ag | Cr | | | 11.3 | ~17 | 74.8 | 8.9 | 3.0 | 47.7 | 50 μm drawdown exhibiting flop from lustrous blue to black |
| | Layer thicknesses [nm] | 41 | 50 | 41 | | | | | | | | | |
| Example 3 | | Cr | Ag | Cr | | | 9.6 | ~17 | 45.4 | 4.1 | 1.9 | 53.9 | 50 μm drawdown exhibiting flop from lustrous red to black |
| | Layer thicknesses [nm] | 32 | 50 | 32 | | | | | | | | | |
| Example 4 | | Cr | Ag | Cr | | | 10.2 | 20 | 44.6 | 3.9 | 1.9 | 53.9 | 50 μm drawdown exhibiting flop from lustrous violet to black |
| | Layer thicknesses [nm] | 38 | 50 | 38 | | | | | | | | | |
| Example 5 | | Cr | Al | Cr | | | 4.6 | 17 | 92 | 22.7 | 13.9 | 23 | 50 μm drawdown with brown luster |
| | Layer thicknesses [nm] | 24 | 60 | 24 | | | | | | | | | |
| Example 6 | | Cr | Al | Cr | | | 6.9 | 18 | 69 | 9.15 | 3.8 | 41 | 36 μm drawdown with blue luster |
| | Layer thickness [nm] | 40 | 50 | 40 | | | | | | | | | |
| Example 7 | | Cr | Al | Cr | Measurement of individual layers | | 4.6 | ~17 | 101 | 16 | 6 | 39 | 50 μm drawdown with very intense-colored gold luster |
| | REM Layer thickness [nm] | 28 | 40 | 28 | | | | | | | | | |
| | Oxygen $O_2$ [atom %] | 34 | 13 | 34 | | | | | | | | | |
| Example 8 | | Cr | Ag | Cr | | Measurement on the pigment | 14.5 | 24 | 107 | 13.5 | 6.5 | 48 | 50 μm drawdown with very intense-colored gold luster |
| | SEM layer thicknesses [nm] | 25 | 110 | 25 | | | | | | | | | |
| | Oxygen $O_2$ [atom %] | ~35 | ~10 | ~35 | | | | | | | | | |
| Example 9 | | Al | Al | Al | | Measurement on the pigment | | | | | | | Blue pigments |
| | Layer thicknesses [nm] | 72 | 64 | 86 | | | | | | | | | |
| | Oxygen $O_2$ [atom %] | 48 | 30 | 48 | | | | | | | | | |

TABLE 5-continued

| Sample | Layer sequence of vapor-deposited metal | | | Measurement methodology | | Level of pigmentation [%] | D 50: [μm] | Lightnesses | | | Flop | Subjective perceived color |
|---|---|---|---|---|---|---|---|---|---|---|---|---|
| | | | | EDX | ESCA | | | L15 | L45 | L110 | | |
| Example 10 | | Al | Al | Al | Measure- | | 4.3 | 22 | 105 | 21 | 12.1 | 31 | Pigments with gold- |
| | SEM layer thicknesses [nm] | 38 | 100 | 38 | ment of individual layer and | | | | | | | | colored appearance |
| | Oxygen O$_2$ [atom %] | 50 | 18 | 55 | on the pigment | | | | | | | | |
| | | Al | Al | Al | | | | | | | | | |
| | SEM layer thicknesses [nm] | ~50 | 50 | ~50 | | | | | | | | | |
| | Oxygen O$_2$ [atom %] | 40 | 20 | 40 | | | | | | | | | |
| Example 12 | | Cr | Al | Cr | | | ~4 | ~17 | 101 | 12 | 5.4 | 51 | 50 μm drawdown exhibiting flop from pale gold luster to dark |
| | Layer thicknesses [nm] | ~15 | ~40 | ~15 | | | | | | | | | |
| Example 13 | | | Al | | | | 9 | 24 | 49 | 3.84 | 2.11 | 61 | 50 μm black draw-down exhibiting red/ blue flop |
| | SEM layer thicknesses [nm] | | 252 | | | | | | | | | | |
| Example 20 | | Fe/Cr | Al | Fe/Cr | Measure- | | | | | | | | Very intense-colored gold magnetic color pigments |
| | SEM layer thicknesses [nm] | 40 | 40 | 40 | ment of individual layers | | | | | | | | |
| | Oxygen O$_2$ [atom %] | 53 | 17 | 52 | | | | | | | | | |
| Example 21 | | Ti | Al | Ti | Measure- | | | | | | | | Color pigments with blue luster |
| | SEM layer thicknesses [nm] | 50 | 60 | 50 | ment of individual layers | | | | | | | | |
| | Oxygen O$_2$ [atom %] | 66 | 17 | 66 | | | | | | | | | |
| Example 22 | | Cr | Cr | Cr | Measure- | | | | | | | | Color pigments with lustrous turquoise color |
| | SEM layer thicknesses [nm] | 40 | 70 | 40 | ment of individual layers | | | | | | | | |
| | Oxygen O$_2$ [atom %] | 44 | 59.6 | 44 | | | | | | | | | |
| Example 23 | | Ag | Ag | Ag | Measure- | | | 12.2 | | | | | Color pigments with lustrous pale gold color |
| | SEM layer thicknesses [nm] | 20 | 21 | 19 | ment of individual layers | | | | | | | | |
| | Oxygen O$_2$ [atom %] | 11 | 9 | 11 | | | | | | | | | |
| Example 24 | | Cu | Cu | Cu | Measure- | | | 8.6 | | | | | Color pigments with lustrous violet-copper color |
| | SEM layer thicknesses [nm] | 43 | 43 | 37 | ment of individual layers | | | | | | | | |
| | Oxygen O2 [atom %] | 23 | 19 | 24 | | | | | | | | | |

Characterization by Electron Diffraction

On selected samples, TEM micrographs (instrument: Scanning Transmission electron microscope, manufacturer: Jeol (Japan), type: 2010) were produced. The prepared cross section of the samples was irradiated in transmission with an electron beam of 200 keV, and the structure images and also the diffraction images were recorded using a CCD camera. In light image regions, the electron beam is not greatly scattered, while darker regions are caused by a high level of interaction of the electrons with the sample. The effects involved may be not only scattering on dense and heavy regions, but also diffraction effects at crystal surfaces.

Evaluation of the diffractograms provides information on the crystallographic structure of the sample. Where the electron beam strikes a single crystal, it is diffracted at the network planes of the crystal, and generates a discrete diffraction spectrum in the focal plane of the TEM. Where the imaged region is composed of numerous small, randomly oriented crystallites (polycrystalline material), then, instead of individual diffraction points, concentric circles are formed, the Debye-Scherrer rings. In the case of amorphous samples, the diffraction pattern is composed of diffuse rings. These structures are specific to each material and for numerous substances are documented in the literature.

The following samples were characterized by means of electron diffraction, by way of example, for further characterization of the layer A or C of the pigments according to the invention:

Example 7

Cr—Al—Cr inventive pigment with total layer sequence

Example 18 individual layer of Cr (layer A): in the course of the preparation of example 7, the first layer A was isolated after only single vapor-coating of the release coat with Cr in an oxygen-containing environment.

Example 19 single layer of Al (layer A): in the course of the preparation of example 10, only the first layer A (Al in oxygen-containing environment) was applied in isolation in the single-stage vapor-coating process to part of the release coat, by a skilful choice of shutters (see FIG. 11), and later parted separately from the film.

Sample Preparation:

The samples were incorporated into an epoxy resin. After curing, slices with a thickness of about 100 nm were prepared by means of Ultramicrotomy, and were applied to TEM grids.

Evaluation:

The prepared TEM specimens were illuminated in transmission with an electron beam of 200 kV. By imaging of the focal plane, the diffraction patterns of the samples irradiated in transmission with electron beams were visualized. In this case, for the individual layer of example 18, two distinct rings were detected as diffraction signals (CCD camera).

In the case of the sample from example 7, sharp reflections and also rings were detected. The position of the individual reflections and rings is compared with characteristic diffraction constants from the literature. Table 6 sets out the experimental values (only the most intense signals are evaluated), literature data, and assignments of the experimental data.

ited Cr is present both in an extremely finely divided (nanometric) metallic form and in an oxide form.

If the layer was purely oxidic in character, then no signals corresponding to the metallic chromium should have been detected.

In the sense of this invention, nevertheless, this layer is largely homogeneous in composition, since phases of this kind which exist on one nanometer plane can no longer be resolved by the other methods (EDX, XPS).

Evidently the metallic chromium and the oxidic chromium are also largely mixed with one another to form a layer, and do not take the form, for instance, of two separate, successive layers, since in that case corresponding concentration differences would have been detected by the other measurement method.

In the case of example 7, in addition to the ring signals from example 18, sharp reflections were detected which can be assigned to the metallic aluminum of the middle layer B.

In the case of example 19, reflections were obtained which can be assigned unambiguously to metallic aluminum. In the diffractogram, however, weak ring structures were also detectable. There were no signals found that might have corresponded to crystalline aluminum oxides. Here, evidently, therefore, metallic aluminum particles are present which are embedded in amorphous layer of aluminum oxide. The size of these metallic aluminum particles is larger than that of the chromium particles in example 18, since here there are reflections as well as ring structures. The size there is in a range from 10 to 20 nm.

TABLE 6

Results of electron diffraction experiments

| Sample | d (Å) measured | Reflection character | Assignment | Literature values d (Å) | rel. intensity |
|---|---|---|---|---|---|
| Example 18 | 2.488 | Ring 1 | $Cr_2O_3$ (layer A) | Cr (metal): | |
| | 2.56 | Ring 1 | $Cr_2O_3$ (layer A) | 2.039 | 100 |
| | 2.072 | Ring 2 | Cr (layer A) | $Cr_2O_3$: | |
| | 2.089 | Ring 2 | Cr (layer A) | 2.665 | 100 |
| | | | | 2.480 | 93 |
| Example 7 | 2.326 | Reflection 1 | Al (layer B) | Cr (metal): | |
| | 2.320 | Reflection 2 | Al (layer B) | 2.039 | 100 |
| | 2.020 | Reflection 3 | Al (layer B) | $Cr_2O_3$: | |
| | 2.019 | Reflection 4 | Al (layer B) | 2.665 | 100 |
| | 2.488 | Ring 1 | $Cr_2O_3$ (layer A/C) | 2.480 | 93 |
| | 2.56 | Ring 1 | $Cr_2O_3$ (layer A/C) | Al (metal): | |
| | 2.072 | Ring 2 | Cr (layer A/C) | 2.338 | 100 |
| | 2.089 | Ring 2 | Cr (layer A/C) | 2.024 | 47 |
| Example 19 | 2.349 | Reflection 1 | Al (layer A) | Al (metal): | |
| | 2.339 | Reflection 2 | Al (layer A) | 2.338 | 100 |
| | 2.043 | Reflection 3 | Al (layer A) | 2.024 | 47 |

In the case of example 18, only two rings and no sharp reflections were detectable. This result shows that crystalline structures are present in a size range of below 10 nm.

When comparing the lattice constants calculated from the position of the rings with the literature values for elemental chromium and also for $Cr_2O_3$, it is found that ring 1 can be assigned to $Cr_2O_3$ and ring 2 to metallic Cr. In this one layer, therefore, which represents an example of the layers A and/or C of the metallic effect pigments of the invention, the depos-

Examples of Cosmetic Formulations

Inventive Example 25

Nail Varnish Composition

Beforehand the pigment suspension from example 8 is rewetted in ethyl acetate and adjusted to a solids content of 20% by weight.

TABLE 7

Nail varnish composition

| No. | Substance | Concentration in % by weight |
|---|---|---|
| 1 | Inventive example 8: (20% by weight metallic effect pigment in ethyl acetate) | 20 |
| 2 | Hostaphat CS 120* | 1 |
| 3 | Methyl ethyl ketone | 20 |
| 4 | Methyl isobutyl ketone | 20 |
| 5 | CAB 381.2 | 9 |
| 6 | Butyl acetate 98/100 | 30 |

*Stearylphosphoric ester

Preparation:

The pigment suspension of inventive example 8 was brought to a pigment content of 25% by weight by cautious evaporation of acetone. The butyl acetate is introduced and the CAB (cellulose acetylbutyrate) powder is added in portions with stirring.

Components 2-4 are added in succession to the metal pigment dispersion and gently incorporated.

This gives a nail varnish which, following application to a fingernail, leaves behind an intense gold-metallic impression.

Inventive Example 26

Lip Gloss

The pigment suspension from example 8 is rewetted beforehand in isononyl nonanoate and adjusted to a solids content of 20% by weight.

| INCI Name | Product Name | % W/W | Supplier |
|---|---|---|---|
| A | | 100.00 | |
| Hydrogenated polyisobutene (and) ethylene/propylene/styrene copolymer (and) butylene/ethylene/styrene copolymer | Versagel ME 750 | 74.10 | www.penreco.com |
| Simmondsia Chinensis (Jojoba) seed oil | Jojoba Oil - Natural/Golden | 2.00 | www.biochemica.com |
| Caprylyltrimethicone | Silcare Silicone 31M50 | 7.00 | www.clariant.com |
| Stearyldimethicone | Silcare Silicone 41M65 | 3.20 | www.clariant.com |
| Hydrogenated polydecene | Nexbase 2002 | 4.00 | www.jandekker.com |
| Isopropyl myristate | Isopropyl Myristate | 4.50 | www.vwr.com |
| B | | | |
| Inventive example 8: (20% by weight metallic effect pigment in isononyl nonanoate) | — | 5.00 | |
| Propylparaben | Propyl 4-hydroxybenzoate | 0.20 | www.sigmaaldrich.com |

Preparation Process:
1. Phase A is heated to 85° C.
2. Phase B is added to phase A and the phases are mixed until homogeneity is obtained
3. A lip-gloss container is filled This gives a lip gloss which, following application to the lips, leaves behind a gold-metallic impression.

Inventive Example 27

Lipstick

| INCI Name | Product Name | % W/W | Supplier |
|---|---|---|---|
| A | | 100.00 | |
| Carnauba wax | Ewacera 34 | 5.04 | www.wagnerlanolin.de |
| Beeswax | Ewacera 12 | 3.92 | www.wagnerlanolin.de |
| Candelilla wax | Ewacera 42 | 4.48 | www.wagnerlanolin.de |
| Microcrystalline wax | Parcera MW | 8.07 | www.paramelt.com |
| Cetyl palmitate | Walrath synthetic | 2.24 | www.kahlwax.de |
| Hydrogenated coco-glyceride | Softisan 100 | 5.60 | www.sasolwax.com |
| Petrolatum | Penreco Blond | 6.50 | www.penreco.com |
| Cetearyl octanoate | Luvitol EHO | 11.99 | www.basf.com |
| Tocopheryl acetate | D,L-alpha-Tocopherol acetate | 0.56 | www.dsm.com |
| Castor oil | Castor Oil | 44.37 | www.riedeldehaen.com |

| INCI Name | Product Name | % W/W | Supplier |
|---|---|---|---|
| B | | | |
| Inventive example 8: (20% by weight metallic effect pigment in isononyl nonanoate) | — | 7.00 | |
| Methylparaben, Propylparaben | Rokonsal SSH-1 | 0.22 | www.biochema.com |

Preparation Process:
1. Phase A is heated to 85° C.
2. Phase B is added to phase A and the phases are mixed
3. A lipstick mold is filled at 75° C.

This produces a lipstick which, following application to the lips, leaves behind a gold-metallic impression.

Inventive Example 28

Liquid Eyeliner

| INCI Name | Product Name | % W/W | Supplier |
|---|---|---|---|
| A | | 100.00 | |
| Water | Aqua | 64.70 | |
| Water/carbon dispersion | MBD 201 | 3.00 | www.geotech.nl |
| Acrylate copolymer | Covacryl E14 | 10.00 | www.lcw.fr |
| Magnesium aluminum silicate | Veegum HV | 1.00 | www.cherbsloeh.de |
| B | | | |
| Propylene glycol | 1,2 propanediol | 3.00 | www.vwr.com |
| Triethanolamine | Triethanolamine | 1.40 | www.vwr.com |
| C | | | |
| Xanthan gum | Keltrol T | 0.30 | www.cpkelco.com |
| D | | | |
| Mica | Silk Mica | 2.00 | www.vwr.com |
| E | | | |
| Inventive example 8: (20% by weight metallic effect pigment in isononyl nonanoate) | — | 5.00 | |
| Stearic acid | Kortacid 1895 | 2.80 | www.akzonobel.de |
| Glyceryl stearate | Aldo MS K FG | 0.80 | www.lonza.com |
| Oleyl alcohol | HD-Ocenol 90/95 V | 0.50 | www.biesterfeld.com |
| Phenoxyethanol (and) methylparaben (and) ethylparaben (and) butylparaben | Uniphen P-23 | 0.50 | www.induchem.com |
| F | | | |
| Dimethicone (and) trisiloxane | Dow Corning 2-1184 Fluid | 5.00 | www.dowchemicals.com |

Preparation Process:
1. Dispersing of Veegum in phase A
2. Stirring for 15 minutes.
3. Phase B is added to phase A
4. Phase C is added to phase AB
5. Stirring for 10 minutes
6. Phase D is added to phase ABC and heated to 75° C.
7. Phase E is heated to 75° C.
8. Phase E is added to phase ABCD
9. Cooling to 60° C. and addition of phase F
10. Pouring into an appropriate container This produces a liquid eyeliner which, following application to the eyelid, leaves behind a gold-metallic impression.

KEY

FIG. 3:
1. Vaporization source
2. Prepared rotary plate
3. Shutter
4. Fixed oscillating quartz
5. Vacuum chamber
6. Axis of rotation FIG. 4a:
1. Release-coated source roll
2. and 3. Deflection roll
4. Roll take-up device
5. and 6. Transmittance measurement
7. Oscillating quartz measurement
8. Vaporizer boat
9. and 10. Shutter entrance and shutter exit

FIG. 4b:

1. Release-coated source roll
2. and 3. Deflection roll
4. Roll take-up device
5. and 6. Transmittance measurement
7. Oscillating quartz measurement
8. Vaporizer boat A, B, and C
9, 10, 11, and 12. Partition walls
FIG. 9:
1. Oxygen source 1
2. Oxygen source 2
3. Metal vaporization source
FIG. 15:
1. Oxygen source
2. Metal vaporization source

What is claimed is:

1. A metallic effect pigment wherein
the metallic effect pigment comprises at least three layers:
A) a layer A which consists of at least one metal $M_A$ and has an average oxygen content $O_A$, based on the total amount of $M_A$ and $O_A$ in the layer A,
B) a layer B comprising at least one metal $M_B$ and having an average oxygen content $O_B$ of 0 to 77 atom %, based on the total amount of $M_B$ and $O_B$ in the layer B,
C) a layer C which consists of at least one metal $M_C$ and has an average oxygen content $O_C$, based on the total amount of $M_C$ and $O_C$ in the layer C,
wherein the at least one of metal$_A$ and metal $M_C$ is selected from the group consisting of aluminum, magnesium, chromium, silver, copper, gold, zinc, tin, manganese, iron, cobalt, nickel, titanium, tantalum, molybdenum, mixtures thereof and alloys thereof, and
wherein the at least one of layer A and layer C comprises different phases of metal and metal oxide in finely divided form,
the average oxygen content $O_{AC}$ in layers A and C being determined in accordance with the formula (I)

$$O_{AC} = \frac{1}{2}\left(\frac{O_A}{M_A + O_A} + \frac{O_C}{M_C + O_C}\right) \quad (I)$$

and being situated within a range from 2 to 77 atom %, wherein each of layer A and layer C is not a pure, stoichiometric oxide layer and wherein layers A, B and C are arranged immediately following one another.

2. The metallic effect pigment of claim 1, wherein
at least one of the layers A and C have a homogeneous chemical composition in terms of at least one of oxygen $O_A$ and $O_C$ and at least one of metal $M_A$ and $M_C$, respectively.

3. The metallic effect pigment of claim 1, wherein
layers A and C of the metallic effect pigment have an average oxygen content $O_{AC}$ of 30 to 57 atom %.

4. The metallic effect pigment of claim 1, wherein
layers A and C of the metallic effect pigment have an average oxygen content $O_{AC}$ of 35 to 56 atom %.

5. The metallic effect pigment of claim 1, wherein
in at least one of layers A and C of the metallic effect pigment, the total amount of $M_A$ and of $O_A$ is 90 to 100 atom %, based on all of the components of the layer A, and the total amount of $M_C$ and of $O_C$ is 90 to 100 atom %, based on all of the components of the layer C.

6. The metallic effect pigment of claim 1, wherein
the average oxygen content $O_A$, based on the total amount of $M_A$ and $O_A$ in the layer A, and the average oxygen content $O_C$, based on the total amount of $M_C$ and $O_C$ in the layer C, are each situated independently of one another in a range from 25 to 58 atom %.

7. The metallic effect pigment according to claim 6, wherein the average oxygen content $O_A$, based on the total amount of $M_A$ and $O_A$ in the layer A, and the average oxygen content $O_C$, based on the total amount of $M_C$ and $O_C$ in the layer C are each situated independently of one another in a range from 30 to 57 atom %.

8. The metallic effect pigment of claim 1, wherein
the at least one of layer A and C independently of one another possess an average thickness of 10 to 250 nm.

9. The metallic effect pigment of claim 1, wherein
the at least one metal $M_B$ is selected from the group consisting of aluminum, chromium, silver, copper, gold, zinc, tin, manganese, iron, cobalt, nickel, titanium, mixtures thereof, and alloys thereof.

10. The metallic effect pigment of claim 1, wherein
the average oxygen content $O_B$, based on the total amount of $M_B$ and $O_B$ in the layer B, is situated in a range from 0 to less than 25 atom %.

11. The metallic effect pigment of claim 10, wherein
the layer B has a metallic character and possesses an average thickness of 10 to 200 nm.

12. The metallic effect pigment of claim 1, wherein
the average oxygen content $O_B$, based on the total amount of $M_B$ and $O_B$ in the layer B, is situated at 25 to 58 atom %.

13. The metallic effect pigment of claim 12, wherein
the layer B has a largely metallic or oxidic character and possesses an average thickness of 50 to 2000 nm.

14. The metallic effect pigment of claim 1, wherein
the overall metallic effect pigment possesses an average thickness of 30 to 550 nm.

15. The metallic effect pigment of claim 14, wherein
the overall metallic effect pigment possesses an average thickness of 50 to 300 nm.

16. The metallic effect pigment of claim 1, wherein
the metal $M_B$ is at least one of aluminum and silver.

17. The metallic effect pigment of claim 1, wherein
the metals $M_A$ and $M_C$ are the same.

18. The metallic effect pigment of claim 1, wherein
the metals $M_A$, $M_B$, and $M_C$ are the same.

19. The metallic effect pigment of claim 1, wherein
the average layer thicknesses of layers A and C are substantially the same.

20. The metallic effect pigment of claim 1, wherein
at least one of said metal $M_A$ and $M_C$ is substantially chromium and in at least one of said layer A and C independently of one another the average oxygen content $O_A$ or $O_C$ is situated in the range from 35 to 48 atom %, based on the respectively total amount of chromium and oxygen in layer A and C, respectively.

21. The metallic effect pigment of claim 1, wherein
at least one of said metal $M_A$ and $M_C$ is substantially aluminum and in at least one of said layer A and C independently of one another the average oxygen content $O_A$ or $O_C$ is situated in the range from 30 to 55 atom %, based on the respectively total amount of aluminum and oxygen in layer A and C, respectively.

22. The metallic effect pigment of claim 1, wherein
the metallic effect pigment is coated with an anticorrosion layer.

23. The metallic effect pigment of claim 22, wherein
the anticorrosion layer comprises $SiO_2$.

24. The metallic effect pigment of claim 22, wherein the metallic effect pigment is envelopingly coated with an anticorrosion layer.

25. The metallic effect pigment of claim 23, wherein the anticorrosion layer consists of $SiO_2$.

26. A process for preparing a metallic effect pigment of claim 1, wherein
the individual layers A, B, and C are arranged in succession by PVD techniques, by vapor deposition of $M_A$, $M_B$, and $M_C$, with at least one of said layers A and C being vapor-deposited in the presence of at least one oxygen-donating oxygen source.

27. The process according to claim 26 for preparing a metallic effect pigment, wherein
the process comprises the following steps:
a) coating a mobile substrate in a vacuum chamber by physical vapor deposition (PVD) with at least one metal $M_A$ in the presence of oxygen, to form the layer A on the substrate,
b) coating the layer A in a vacuum chamber by physical vapor deposition (PVD) with at least one metal $M_B$ in the presence or absence of oxygen, to form the layer B,
c) coating the layer B in a vacuum chamber by physical vapor deposition (PVD) with at least one metal $M_C$ in the presence of oxygen, to form the layer C,
d) detaching the metallic layer stack from the substrate,
e) comminuting the metallic layer stack to give metallic effect pigments, and
f) optionally converting the metallic effect pigments into a dispersion or paste.

28. The process according to claim 26 for preparing a metallic effect pigment, wherein
the process comprises the following steps:
a) coating a substrate in a vacuum chamber with at least the metal $M_A$ from a vaporizer source $VQ_A$ in the presence of an oxygen-donating oxygen source, to form the layer A,
b) coating the layer A on the substrate, in a vacuum chamber with at least the metal $M_B$ from a vaporizer source $VQ_B$ in the presence or absence of an oxygen source, to form the layer B,
c) coating the layer B on the substrate, in a vacuum chamber with at least the metal $M_C$ from a vaporizer source $VQ_C$ in the presence of an oxygen source, to form the layer C,
d) detaching the metallic layer stack from the substrate,
e) comminuting the metallic layer stack to form metallic effect pigments, and
f) optionally converting the metallic effect pigments into a dispersion or a paste.

29. The process according to claim 28 for preparing a metallic effect pigment, wherein the substrate is a mobile substrate.

30. The process according to claim 29 for preparing a metallic effect pigment, wherein the mobile substrate is a circulating belt or a moving belt.

31. The process according to claim 28 for preparing a metallic effect pigment, wherein
the individual vaporizer sources $VQ_A$, $VQ_B$, and $VQ_C$ are separate from one another or separate in each case in pairs from one another.

32. The process according to claim 26 for preparing a metallic effect pigment, wherein
$M_A$, $M_B$, and $M_C$ are identical, identical in pairs or different from one another, and, from at least one metal vaporizing source and wherein a mobile substrate is coated with metal in a vacuum chamber in the presence of one or more oxygen-donating oxygen sources, accompanied by formation, between the metal vaporizing source, the oxygen source, and the mobile substrate, of three-dimensional concentration regions of metal vapor and oxygen in the vacuum chamber, as a result of which, by physical vapor deposition, the at least three layers A, B, and C are deposited on the mobile substrate in succession with metal contents and oxygen contents that are distinguishable from one another.

33. The process according to claim 32 for preparing a metallic effect pigment, wherein
at least one cover device is arranged between a metal vaporization source, oxygen source, and mobile substrate, said at least one device suppressing the possible formation of transition layers between the layers A, B, and C, with the consequence that the at least three successive layers A, B, and C are deposited each with mutually distinguishable metal and oxygen contents.

34. The process according to claim 32 for preparing a metallic effect pigment, wherein the mobile substrate is a rotating belt or a moving belt.

35. The process according to claim 26 for preparing a metallic effect pigment, wherein
the at least one oxygen source is disposed in the form of at least one of water, water-donating substances, oxygen-donating substances and oxygen gas in the vacuum chamber.

36. The process according to claim 26 for preparing a metallic effect pigment, wherein
during step a) and step c), and optionally during step b), there is controlled metering of oxygen gas into the vacuum chamber.

37. A method of making a material selected from the group consisting of coatings, paints, automobile finishes, powder coatings, printing inks, digital-printing inks, plastics and cosmetic formulations, wherein the method comprises combining the material with a quantity of the metallic effect pigments of claim 1.

38. A coating composition wherein
the coating composition comprises metallic effect pigments of claim 1.

39. The coating composition of claim 38, wherein
the coating composition is selected from the group consisting of coatings, paints, automobile finishes, powder coatings, printing inks, digital-printing inks, plastics, and cosmetic formulations.

40. A coated article wherein the article is provided with a coating composition according to claim 38.

41. A coated article wherein
the article is provided with the metallic effect pigments of claim 1.

42. The metallic effect pigment according to claim 1, wherein the layer B has an average oxygen content $O_B$ of 0 to 58 atom %.

43. The metallic effect pigment according to claim 1, wherein the average oxygen content $O_{AC}$ in layers A and C is situated within a range from 25 to 58 atom %.

44. The metallic effect pigment of claim 1, wherein said at least layer A and C comprises different phases of metal and metal oxide sized in the nanometer range.

* * * * *